(12) United States Patent
Morgan et al.

(10) Patent No.: US 10,016,198 B2
(45) Date of Patent: Jul. 10, 2018

(54) STAPLES FOR GENERATING AND APPLYING COMPRESSION WITHIN A BODY

(71) Applicant: MX Orthopedics, Corp., Lexington, MA (US)

(72) Inventors: Daniel Morgan, Salem, MA (US); Matthew Palmer, Cambridge, MA (US); Matthew Fonte, Concord, MA (US); Robert Devaney, Auburndale, MA (US); Kaitlyn Nealon, Boston, MA (US); Alexander DelMonaco, Billerica, MA (US)

(73) Assignee: Arthrex, Inc., Naples, FL (US)

( * ) Notice: Subject to any disclaimer, the term of this patent is extended or adjusted under 35 U.S.C. 154(b) by 251 days.

(21) Appl. No.: 15/079,770

(22) Filed: Mar. 24, 2016

(65) Prior Publication Data

US 2016/0199060 A1    Jul. 14, 2016

Related U.S. Application Data

(63) Continuation-in-part of application No. 14/540,351, filed on Nov. 13, 2014, now Pat. No. 9,855,036.

(Continued)

(51) Int. Cl.
*A61B 17/06* (2006.01)
*A61B 17/068* (2006.01)
(Continued)

(52) U.S. Cl.
CPC ........ *A61B 17/0682* (2013.01); *A61B 17/068* (2013.01); *A61B 17/0642* (2013.01);
(Continued)

(58) Field of Classification Search
CPC .................................................. A61B 17/0682
See application file for complete search history.

(56) References Cited

U.S. PATENT DOCUMENTS

| | | |
|---|---|---|
| 2,580,821 A | 1/1952 | Nicola |
| 3,960,147 A | 6/1976 | Murray |

(Continued)

FOREIGN PATENT DOCUMENTS

| | | |
|---|---|---|
| EP | 0826340 A2 | 3/2008 |
| FR | 2787313 A1 | 6/2000 |

(Continued)

OTHER PUBLICATIONS

Cai, S. et al., Texture evolution during nitinol martensite detwinning and phase transformation, Applied Physics Letters 103, 241909 (2013).

(Continued)

*Primary Examiner* — Andrew Yang
(74) *Attorney, Agent, or Firm* — Carlson, Gaskey & Olds P.C.

(57) ABSTRACT

Apparatus for generating, applying and maintaining compression to a site in a human or animal body, the apparatus comprising: a staple comprising: a bridge configured to be elastically bendable; a first leg connected to the bridge by a first hinge region configured to be elastically bendable; and a second leg connected to the bridge by a second hinge region configured to be elastically bendable; wherein the first hinge region comprises a first hole configured to mate with a first element of a delivery device and the second hinge region comprises a second hole configured to mate with a second element of a delivery device; and wherein the first and second legs are angled toward one another when they are in an unstrained state; whereby, when the staple is mounted to a delivery device so that the first hole of the first hinge region mates with a first element of a delivery device and the second hole of the second hinge region mates with a second element of a delivery device, and when the delivery device applies a force to the bridge of the staple so as to (Continued)

reconfigure the bridge of the staple, the first and second legs are pivoted away from one another toward a parallel disposition.

7 Claims, 27 Drawing Sheets

Related U.S. Application Data

(60) Provisional application No. 62/137,496, filed on Mar. 24, 2015, provisional application No. 62/137,570, filed on Mar. 24, 2015, provisional application No. 62/238,472, filed on Oct. 7, 2015.

(51) Int. Cl.
*A61B 17/064* (2006.01)
*A61B 17/00* (2006.01)

(52) U.S. Cl.
CPC ............ *A61B 2017/00867* (2013.01); *A61B 2017/0641* (2013.01); *A61B 2017/0645* (2013.01)

(56) References Cited

U.S. PATENT DOCUMENTS

| | | |
|---|---|---|
| 4,175,555 A | 11/1979 | Herbert |
| 4,428,376 A | 1/1984 | Mericle |
| 4,444,181 A | 4/1984 | Wevers et al. |
| 4,503,569 A | 3/1985 | Dotter |
| 4,512,338 A | 4/1985 | Balko et al. |
| 4,570,623 A | 2/1986 | Ellison et al. |
| 4,733,665 A | 3/1988 | Palmaz |
| 4,858,601 A | 8/1989 | Glisson |
| 4,905,679 A | 3/1990 | Morgan |
| 4,922,905 A | 5/1990 | Strecker |
| 4,950,227 A | 8/1990 | Savin et al. |
| 4,959,064 A | 9/1990 | Engelhardt |
| 4,959,065 A | 9/1990 | Arnett et al. |
| 5,026,390 A | 6/1991 | Brown |
| 5,044,540 A | 9/1991 | Dulebohn |
| 5,061,275 A | 10/1991 | Wallsten et al. |
| 5,089,006 A | 2/1992 | Stiles |
| 5,098,434 A | 3/1992 | Serbousek |
| 5,190,546 A | 3/1993 | Jervis |
| 5,246,443 A | 9/1993 | Mai |
| 5,474,557 A | 12/1995 | Mai |
| 5,607,530 A | 3/1997 | Hall et al. |
| 5,680,981 A | 10/1997 | Mililli et al. |
| 5,766,218 A | 6/1998 | Arnott |
| 5,779,707 A | 7/1998 | Bertholet et al. |
| 5,876,434 A | 3/1999 | Flomenblit et al. |
| 5,947,999 A | 9/1999 | Groiso |
| 6,030,162 A | 2/2000 | Huebner |
| 6,048,344 A | 4/2000 | Schenk |
| 6,187,009 B1 | 2/2001 | Herzog et al. |
| 6,306,140 B1 | 10/2001 | Siddiqui |
| 6,325,805 B1 | 12/2001 | Ogilvie et al. |
| 6,533,157 B1 | 3/2003 | Whitman |
| 6,569,173 B1 | 5/2003 | Blatter et al. |
| 6,607,530 B1 | 8/2003 | Carl et al. |
| 6,623,486 B1 | 9/2003 | Weaver et al. |
| 6,656,184 B1 | 12/2003 | White et al. |
| 6,685,708 B2 | 2/2004 | Monassevitch et al. |
| 6,761,731 B2 | 7/2004 | Majercak |
| 6,773,437 B2 | 8/2004 | Ogilvie et al. |
| 7,175,626 B2 | 2/2007 | Neff |
| 7,229,452 B2 | 6/2007 | Kayan |
| 7,481,832 B1 | 1/2009 | Meridew et al. |
| 7,582,107 B2 | 9/2009 | Trail et al. |
| 7,618,441 B2 | 11/2009 | Groiso |
| 7,625,395 B2 | 12/2009 | Muckter |
| 7,794,483 B2 | 9/2010 | Capanni |
| 7,875,070 B2 | 1/2011 | Molaei |
| 7,955,388 B2 | 6/2011 | Jensen et al. |
| 7,976,648 B1 | 7/2011 | Boylan et al. |
| 7,985,222 B2 | 7/2011 | Gall et al. |
| 7,993,380 B2 | 8/2011 | Hawkes |
| 8,048,134 B2 | 11/2011 | Partin |
| 8,080,044 B2 | 12/2011 | Biedermann et al. |
| 8,114,141 B2 | 2/2012 | Appenzeller et al. |
| 8,118,952 B2 | 2/2012 | Gall et al. |
| 8,137,351 B2 | 3/2012 | Prandi |
| 8,205,782 B2 | 6/2012 | Harari et al. |
| 8,216,398 B2 | 7/2012 | Bledsoe et al. |
| 8,221,478 B2 | 7/2012 | Patterson et al. |
| 8,393,517 B2 | 3/2013 | Milo |
| 8,425,588 B2 | 4/2013 | Molaei |
| 8,486,121 B2 | 7/2013 | Biedermann et al. |
| 8,584,853 B2 | 11/2013 | Knight et al. |
| 8,597,337 B2 | 12/2013 | Champagne |
| 8,721,646 B2 | 5/2014 | Fox |
| 8,790,379 B2 | 7/2014 | Bottlang et al. |
| 8,801,732 B2 | 8/2014 | Harris et al. |
| 8,808,294 B2 | 8/2014 | Fox et al. |
| 8,864,804 B2 | 10/2014 | Champagne et al. |
| 9,017,331 B2 | 4/2015 | Fox |
| 9,095,338 B2 | 8/2015 | Taylor et al. |
| 9,101,349 B2 | 8/2015 | Knight et al. |
| 9,138,274 B1 | 9/2015 | Biesinger et al. |
| 9,204,932 B2 | 12/2015 | Knight et al. |
| 9,326,804 B2 | 5/2016 | Biedermann et al. |
| 9,339,268 B2 | 5/2016 | Fox |
| 9,402,624 B1 | 8/2016 | Scott et al. |
| 9,408,647 B2 | 8/2016 | Cheney |
| 9,451,955 B2 | 9/2016 | Fox |
| 9,451,957 B2 | 9/2016 | Fox |
| 2002/0058940 A1 | 5/2002 | Frigg et al. |
| 2002/0111641 A1 | 8/2002 | Peterson et al. |
| 2002/0198527 A1 | 12/2002 | Muckter |
| 2004/0111089 A1 | 6/2004 | Stevens et al. |
| 2004/0230193 A1 | 11/2004 | Cheung et al. |
| 2004/0260377 A1 | 12/2004 | Flomenblit et al. |
| 2005/0043757 A1 | 2/2005 | Arad et al. |
| 2005/0096660 A1 | 5/2005 | Allen |
| 2005/0152770 A1 | 7/2005 | Tschakaloff et al. |
| 2005/0277940 A1 | 12/2005 | Neff |
| 2005/0288707 A1 | 12/2005 | De Canniere et al. |
| 2006/0264954 A1 | 11/2006 | Sweeney, II et al. |
| 2007/0233124 A1 | 10/2007 | Corrao et al. |
| 2007/0260248 A1 | 11/2007 | Tipirneni |
| 2007/0265631 A1 | 11/2007 | Fox |
| 2007/0270855 A1 | 11/2007 | Partin |
| 2008/0065154 A1 | 3/2008 | Allard et al. |
| 2008/0071373 A1 | 3/2008 | Molz et al. |
| 2008/0132894 A1 | 6/2008 | Coilard-Lavirotte et al. |
| 2008/0234763 A1 | 9/2008 | Patterson et al. |
| 2008/0249574 A1 | 10/2008 | McCombs et al. |
| 2009/0018556 A1 | 1/2009 | Prandi |
| 2009/0105768 A1 | 4/2009 | Cragg et al. |
| 2009/0198287 A1 | 8/2009 | Chiu |
| 2009/0254090 A1 | 10/2009 | Lizee |
| 2009/0264937 A1 | 10/2009 | Parrott |
| 2009/0302089 A1 | 12/2009 | Harari et al. |
| 2010/0036430 A1 | 2/2010 | Hartdegen et al. |
| 2010/0063506 A1 | 3/2010 | Fox et al. |
| 2010/0087822 A1 | 4/2010 | Groiso |
| 2010/0131014 A1 | 5/2010 | Peyrot et al. |
| 2010/0211115 A1 | 8/2010 | Tyber et al. |
| 2010/0237128 A1 | 9/2010 | Miller et al. |
| 2011/0008643 A1 | 1/2011 | Shaw et al. |
| 2011/0060372 A1 | 3/2011 | Allison |
| 2011/0144703 A1 | 6/2011 | Krause et al. |
| 2011/0224725 A1 | 9/2011 | De Canniere et al. |
| 2011/0247731 A1 | 10/2011 | Gordon |
| 2011/0313473 A1 | 12/2011 | Prandi et al. |
| 2012/0116465 A1 | 5/2012 | Elahinia et al. |
| 2013/0030437 A1 | 1/2013 | Fox |
| 2013/0030438 A1 | 1/2013 | Fox |
| 2013/0066435 A1 | 3/2013 | Averous et al. |
| 2013/0123785 A1 | 5/2013 | Fonte |
| 2013/0206815 A1 | 8/2013 | Fox |
| 2013/0231667 A1 | 9/2013 | Taylor et al. |

(56) References Cited

U.S. PATENT DOCUMENTS

| | | |
|---|---|---|
| 2013/0300437 A1 | 11/2013 | Grosjean et al. |
| 2014/0014553 A1 | 1/2014 | Knight et al. |
| 2014/0018809 A1 | 1/2014 | Allen |
| 2014/0020333 A1 | 1/2014 | Knight et al. |
| 2014/0024002 A1 | 1/2014 | Knight et al. |
| 2014/0097228 A1 | 4/2014 | Taylor et al. |
| 2014/0172026 A1 | 6/2014 | Biedermann et al. |
| 2014/0257420 A1 | 9/2014 | Fox |
| 2014/0277516 A1 | 9/2014 | Miller et al. |
| 2014/0324048 A1 | 10/2014 | Fox |
| 2014/0358187 A1 | 12/2014 | Taber et al. |
| 2014/0358247 A1 | 12/2014 | Fox et al. |
| 2015/0133940 A1 | 5/2015 | Palmer et al. |
| 2015/0230843 A1 | 8/2015 | Palmer et al. |
| 2015/0238237 A1 | 8/2015 | Madjarov |
| 2015/0238238 A1 | 8/2015 | Cheney |
| 2016/0051284 A1 | 2/2016 | Cronen |
| 2016/0089190 A1 | 3/2016 | Taber |
| 2016/0095638 A1 | 4/2016 | Reimels |
| 2016/0135808 A1 | 5/2016 | Anderson |
| 2016/0199060 A1 | 7/2016 | Morgan et al. |
| 2016/0235460 A1 | 8/2016 | Wahl |
| 2016/0317202 A1 | 11/2016 | Cheney |
| 2017/0000482 A1 | 1/2017 | Averous et al. |
| 2017/0231625 A1 | 8/2017 | Handie |
| 2017/0252036 A1 | 9/2017 | Palmer et al. |
| 2017/0340777 A1 | 11/2017 | Ma et al. |
| 2017/0347999 A1 | 12/2017 | Palmer et al. |

FOREIGN PATENT DOCUMENTS

| | | |
|---|---|---|
| FR | 2874166 A1 | 2/2006 |
| FR | 2901119 A1 | 11/2007 |
| IL | 64726 A | 2/1985 |
| WO | 2009/091770 A1 | 7/2009 |
| WO | 2014087111 A1 | 6/2014 |

OTHER PUBLICATIONS

Gruszka, Dominik et al., The Durability of the Intrascaphoid Compression of Headless Comperssion Screws: In Vitro Study, The Journal of Hand Surgery, Jun. 2012, pp. 1142-1150.

Huang et al., Ion release from NiTi orthodontic wires in artificial saliva with various acidities, Biomaterials, 24, 2003, pp. 3585-3592.

Supplementary European Search Report for EP Application 14861059.5 dated Sep. 6, 2017.

International Preliminary Report on Patentability for PCT Application No. PCT/US2016/015432 dated Aug. 10, 2017.

International Preliminary Report on Patentability for PCT Application No. PCT/US2014/065406 dated May 17, 2016.

International Preliminary Report on Patentability for PCT Application No. PCT/US2014/065553 dated May 17, 2016.

International Preliminary Report on Patentability for PCT Application No. PCT/US2015/020598 dated Sep. 13, 2016.

International Preliminary Report on Patentability for PCT Application No. PCT/US2015/028328 dated Nov. 1, 2016.

International Search Report and Written Opinion for PCT Application No. PCT/US2014/065406 dated Feb. 24, 2015.

International Search Report and Written Opinion for PCT Application No. PCT/US2014/065553 dated Feb. 24, 2015.

International Search Report and Written Opinion for PCT Application No. PCT/US2015/020598 dated Jun. 12, 2015.

International Search Report and Written Opinion for PCT Application No. PCT/US2015/028328 dated Aug. 4, 2015.

International Search Report and Written Opinion for PCT Application No. PCT/US2016/015432 dated Apr. 21, 2016.

International Search Report and Written Opinion for PCT Application No. PCT/US2016/023980 dated Jul. 21, 2016.

Non-Final Office Action for United States Patent Application No. 14/539,650 dated Apr. 18, 2017.

Non-Final Office Action for U.S. Appl. No. 14/540,351 dated Apr. 19, 2017.

Non-Final Office Action for U.S. Appl. No. 15/650,210 dated Oct. 4, 2017.

Non-Final Office Action for U.S. Appl. No. 15/684,183 dated Oct. 10, 2017.

Supplementary European Search Report for EP Application 14862438.0 dated Jun. 12, 2017.

Supplementary European Search Report for EP Application No. 14861238.5 dated Jun. 12, 2017.

U.S. Appl. No. 14/699,837, filed Apr. 29, 2015, entitled "Controlling the Unloading Stress of Nitinol Devices and/or Other Shape Memory Material Devices".

U.S. Appl. No. 14/539,650, filed Nov. 12, 2014, entitled "Screws for Generating and Applying Compression Within a Body".

U.S. Appl. No. 14/540,351, filed Nov. 13, 2014, entitled "Staples for Generating and Applying Compression Within a Body".

U.S. Appl. No. 15/651,530, filed Jul. 17, 2017, entitled "Staples for Generating and Applying Compression Within a Body".

U.S. Appl. No. 15/650,210, filed Jul. 14, 2017, entitled "Staples for Generating and Applying Compression Within a Body".

U.S. Appl. No. 15/684,183, filed Aug. 23, 2017, entitled "Staples for Generating and Applying Compression Within a Body".

Restriction Requirement for U.S. Appl. No. 14/699,837 dated Sep. 13, 2017.

International Preliminary Report on Patentability for PCT Application No. PCT/US2016/023980 dated Oct. 5, 2017.

STAPLES FOR GENERATING AND APPLYING COMPRESSION WITHIN A BODY

REFERENCE TO PENDING PRIOR PATENT APPLICATIONS

This patent application:

(i) is a continuation-in-part of pending prior U.S. patent application Ser. No. 14/540,351, filed Nov. 13, 2014 by MX Orthopedics, Corp. and Matthew Palmer et al. for STAPLES FOR GENERATING AND APPLYING COMPRESSION WITHIN A BODY (Attorney's Docket No. FONTE-52);

(ii) claims benefit of pending prior U.S. Provisional Patent Application Ser. No. 62/137,496, filed Mar. 24, 2015 by MX Orthopedics, Corp. and Daniel Morgan et al. for STAPLES THAT DO NOT NEED TO BE TAMPED TO BE FULLY SEATED FOR GENERATING AND APPLYING COMPRESSION WITHIN A BODY (Attorney's Docket No. FONTE-55 PROV);

(iii) claims benefit of pending prior U.S. Provisional Patent Application Ser. No. 62/137,570, filed Mar. 24, 2015 by MX Orthopedics, Corp. and Daniel Morgan et al. for STAPLES THAT DO NOT NEED TO BE TAMPED TO BE FULLY SEATED FOR GENERATING AND APPLYING COMPRESSION WITHIN A BODY (Attorney's Docket No. FONTE-56 PROV); and (iv) claims benefit of pending prior U.S. Provisional Patent Application Ser. No. 62/238,472, filed Oct. 7, 2015 by MX Orthopedics, Corp. and Matthew Palmer et al. for DEVICES FOR CONTROLLING THE UNLOADING OF SUPERELASTIC AND SHAPE MEMORY ORTHOPEDIC IMPLANTS (Attorney's Docket No. FONTE-69 PROV).

The four (4) above-identified patent applications are hereby incorporated herein by reference.

FIELD OF THE INVENTION

The present invention relates to staples for generating, applying, and maintaining compression to a site in a human or animal body in order to facilitate healing of diseased or damaged tissue. The invention finds particular utility in the field of orthopedics and specifically for reducing fractures and maintaining compression between bone fragments, and/or for reducing openings and maintaining compression between bone segments in osteotomies, and/or for inducing fusion across the bones of a joint in an arthrodesis. While the invention has application throughout the body, its utility will be illustrated herein in the context of the repair of fractured or displaced bone tissue, such as during an Akin Osteotomy of the foot or an Isolated Lunocapitate Arthrodesis of the hand/wrist.

BACKGROUND OF THE INVENTION

In the field of orthopedic surgery it is common to rejoin broken bones. The success of the surgical procedure often depends on the ability to re-approximate the bone fragments, the amount of compression achieved between the bone fragments, and the ability to sustain that compression over a period of time. If the surgeon is unable to bring the bone fragments into close contact, a gap will exist between the bone fragments and the bone tissue will need to fill that gap before complete healing can take place. Furthermore, gaps between bone fragments that are too large allow motion to occur between the bone fragments, disrupting the healing tissue and thus slowing the healing process. Optimal healing requires that the bone fragments be in close contact with each other, and for a compressive load to be applied and maintained between the bone fragments. Compressive strain between bone fragments has been found to accelerate the healing process in accordance with Wolf's Law.

Broken bones can be rejoined using staples. Staples are formed from a plurality of legs (typically two legs, although sometimes more) connected together by a bridge. Staples are typically manufactured from stainless steel alloys, titanium alloys or Nitinol, a shape memory alloy. The legs of the staples are inserted into pre-drilled holes on either side of the fracture line, with the bridge of the staple spanning the fracture line.

Existing staples need to be impacted so as to make the bottom of the staple bridge sit flush with the bone surface following implantation of the staple legs into the pre-drilled holes. This is because current staples and their associated delivery devices are typically designed to grip the staples under the bridge of the staple. After the staple has been deployed from the delivery device, there is a gap between the bottom of the bridge and the top surface of the bone. A tamp is typically used to fully seat the staple bridge against the bone surface. Thus, an additional step (i.e., the tamping step) is required. In addition, the action of tamping can cause the bone fragments to move out of position, impairing healing.

Furthermore, current staple systems do not allow the surgeon to control the amount of compression that the staple will exert when it is released from the delivery device. While the shape memory and superelastic properties allow Nitinol staples to pull together the opposing bone fragments, the recovery forces and recoverable strain generated by these staples may be too great and may result in the staples "tearing through" the bone tissue and thus not providing a means to generate and maintain compression between the bone fragments.

Additionally, current staple systems do not allow the surgeon to control the rate at which the staple loads the bone when it is removed from the delivery device. Current delivery devices load the bone nearly instantaneously. This may result in a large force impulse as the staple's legs rapidly undergo shape recovery. This force impulse may damage the bone and result in impaired healing.

Current staple systems also do not allow the surgeon to control the extent to which the staple's legs are opened. This can make it particularly difficult to implant the staple into the pre-drilled holes if the holes were drilled slightly out of position. More particularly, if the pre-drilled holes are slightly too close together or slightly too far apart, it may be difficult to fit the staple legs into the holes and may result in impaired healing.

Finally, current staple systems do not allow for the staple to be easily removed following implantation. Since the staples are tamped flush with the bone surface, there is no easy way for surgeons to grip and remove current staples. It is very time-consuming for surgeons to pry out deployed staples and it is difficult to cut deployed staples for removal. In addition, these actions may damage the underlying bone, thus impairing healing and may result in the patient needing to be under anesthesia for a longer period of time.

Thus there exists a significant clinical need for a new staple and a new associated delivery device to implant the staple flush with the bone surface without the need for tamping to fully seat the staple. Additionally, there is a significant clinical need for a staple system that allows the surgeon to control the amount of compression the staple will generate across the fracture line after the staple has been implanted into bone, to control the rate at which the staple loads the bone, to allow the surgeon to adjust opening the staple legs for proper alignment with pre-drilled holes, and to allow the staple to be easily removed from the bone if desired.

SUMMARY OF THE INVENTION

The present invention provides a novel fixation device which is able to bring bone fragments into close proximity with each other, generate a compressive load across a fracture line and maintain that compressive load across the fracture line while healing occurs.

Among other things, the present invention comprises the provision and use of a novel staple which is manufactured from a shape memory material (e.g., a material capable of exhibiting superelasticity and/or a temperature-induced shape change). The shape memory material may comprise a metal alloy (e.g., Nitinol) or a polymer (e.g., appropriately processed PEEK). Alternatively, the novel staple may be manufactured from another suitable material, e.g., stainless steel, titanium, etc. The staple is designed to reduce fractures and generate and maintain compression across a fracture line between the bone fragments to aid in fracture healing. Note that in the preferred form of the invention, the staple is designed to generate and maintain compression between both the cortical bone and the cancellous bone of the bone fragments so as to promote effective healing.

In one form of the invention, the staple comprises an elastic bridge and two elastic legs. The bridge and the legs meet at a pair of curved hinge regions which are also elastic. The hinge regions comprise holes that run through the full thickness of the hinge regions and are used to mate the staple to a delivery device. In the unrestrained state, the legs of the staple are oriented inwardly with an angle of less than 90° (relative to the bridge) and the bridge of the staple is bowed upward. Prior to implantation, the bridge of the staple can be reversibly bent and the legs of the staple can be reversibly pivoted (e.g., by bending at the elastic hinge regions) so that the bridge is more linear and the legs are substantially perpendicular to the longitudinal axis of the bridge. This allows for insertion of the staple into a prepared fracture site. A delivery device that mates with the holes in the staple's hinge region may be used to strain the staple, or the delivery device may act as a constraint, with the staple being strained while not loaded on the delivery device and then loaded onto the delivery device in the strained state. The constrained staple can then be inserted into the prepared fracture site (e.g., by positioning the staple's legs into pre-drilled holes on either side of the fracture line) and the staple can be released from the delivery device. Since the delivery device engages the staple at the holes in the hinge region, the staple can be fully seated during implantation (i.e., the bottom of the bridge can sit on the surface of the bone) and does not need to be tamped in order to fully seat the staple. Releasing the staple from the delivery device allows the bridge and legs of the staple to attempt to return to their original unrestrained state, thereby generating and maintaining a compressive load while healing occurs.

In one preferred form of the invention, there is provided apparatus for generating, applying and maintaining compression to a site in a human or animal body, the apparatus comprising:
a staple comprising:
a bridge configured to be elastically bendable;
a first leg connected to the bridge by a first hinge region configured to be elastically bendable; and
a second leg connected to the bridge by a second hinge region configured to be elastically bendable;
wherein the first hinge region comprises a first hole configured to mate with a first element of a delivery device and the second hinge region comprises a second hole configured to mate with a second element of a delivery device; and
wherein the first and second legs are angled toward one another when they are in an unstrained state;
whereby, when the staple is mounted to a delivery device so that the first hole of the first hinge region mates with a first element of a delivery device and the second hole of the second hinge region mates with a second element of a delivery device, and when the delivery device applies a force to the bridge of the staple so as to reconfigure the bridge of the staple, the first and second legs are pivoted away from one another toward a parallel disposition.

In another preferred form of the invention, there is provided a method for generating, applying and maintaining compression to a site in a human or animal body, the method comprising:
providing a staple comprising:
a bridge configured to be elastically bendable;
a first leg connected to the bridge by a first hinge region configured to be elastically bendable; and
a second leg connected to the bridge by a second hinge region configured to be elastically bendable;
wherein the first hinge region comprises a first hole configured to mate with a first element of a delivery device and the second hinge region comprises a second hole configured to mate with a second element of a delivery device; and
wherein the first and second legs are angled toward one another when they are in an unstrained state;
providing a delivery device comprising:
a first element sized to be received in the first hole of the first hinge region of the staple;
a second element sized to be received in the second hole of the second hinge region of the staple; and
a plunger adapted to apply a force to the bridge of the staple so as to reconfigure the bridge of the staple;
mounting the staple to the delivery device so that the first hole of the first hinge region mates with the first element of the delivery device and the second hole of the second hinge region mates with the second element of the delivery device;
applying a force to the bridge of the staple with the plunger of the delivery device so as to reconfigure the bridge of the staple such that the first and second legs are pivoted away from one another toward a parallel disposition;
inserting the staple into a site in a human or animal body;
withdrawing the plunger of the delivery device from the bridge of the staple so as to cause the staple to apply compression to the site in a human or animal body as the staple reconfigures; and
releasing the staple from the delivery device.

In another preferred form of the invention, there is provided a staple comprising:
a bridge configured to be elastically bendable;
a first leg connected to the bridge by a first hinge region configured to be elastically bendable; and
a second leg connected to the bridge by a second hinge region configured to be elastically bendable;
wherein the first hinge region comprises a first hole and the second hinge region comprises a second hole; and wherein the bridge has a non-linear configuration when it is in an unstrained state, and wherein the first and second legs are angled toward one another when they are in an unstrained state.

In another preferred form of the invention, there is provided apparatus for securing tissue to a site in a human or animal body, the apparatus comprising:
a staple comprising:
a bridge configured to be elastically bendable;
a first leg connected to the bridge by a first hinge region configured to be elastically bendable; and
a second leg connected to the bridge by a second hinge region configured to be elastically bendable;
wherein the first hinge region comprises a first hole and the second hinge region comprises a second hole; and
wherein the bridge has a non-linear configuration when it is in an unstrained state, and wherein the first and second legs are angled toward one another when they are in an unstrained state; and
at least one suture extending through (i) at least one of the first hole and the second hole, and (ii) the tissue to be secured to the site in a human or animal body.

In another preferred form of the invention, there is provided a staple comprising:
a bridge configured to be plastically deformable;
a first leg connected to the bridge by a first hinge region configured to be elastically bendable; and
a second leg connected to the bridge by a second hinge region configured to be elastically bendable;
wherein the first hinge region comprises a first hole and the second hinge region comprises a second hole; and
wherein the bridge has a non-linear configuration when it is in an unstrained state, and wherein the first and second legs are angled toward one another when they are in an unstrained state.

In another preferred form of the invention, there is provided a staple comprising:
a bridge configured to be elastic;
a first leg connected to the bridge by a first hinge region configured to be elastically bendable; and
a second leg connected to the bridge by a second hinge region configured to be elastically bendable;
wherein the first hinge region comprises a first hole and the second hinge region comprises a second hole; and
wherein the first and second legs are angled toward one another when they are in an unstrained state.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 11 shows the staple in its unstrained condition, FIG. 12 shows the staple strained with its bridge elastically bent (i.e., made to be more concave) and its legs pivoted outwards (e.g., by bending at the elastic hinge regions) so as to be perpendicular to the bridge, and FIG. 13 is a schematic view showing how the elastically bent staple of FIG. 12 will have its legs "kick inward" when the strain on the staple is removed;

FIG. 14 shows the staple in its unstrained condition, FIG. 15 shows the staple strained with its bridge elastically bent (i.e., made to be more sloped) and its legs pivoted outwards (e.g., by bending at the elastic hinge regions) so as to be parallel with each other, and FIG. 16 is a schematic view showing how the elastically bent staple of FIG. 15 will have its legs "kick inward" when the strain on the staple is removed;

FIG. 17 shows the staple in its unstrained condition, FIG. 18 shows the staple strained with its bridge elastically bent (i.e., made to be more linear) and its legs pivoted outwards (e.g., by bending at elastic hinge regions) so as to be perpendicular to the bridge, and FIG. 19 is a schematic view showing how the elastically bent staple of FIG. 18 will have its legs "kick inward" when the strain on the staple is removed;

—FIG. 20 shows the staple in its unstrained condition, FIG. 21 shows the staple strained with its malleable bridge plastically bent (i.e., made to take a set so as to be concave to match the fracture site anatomy) and its legs pivoted outwards (e.g., by bending at elastic hinge regions) so as to be perpendicular to the bridge, and FIG. 22 is a schematic view showing how the elastically bent staple of FIG. 21 will have its legs "kick inward" when the strain on the staple is removed.

DETAILED DESCRIPTION OF THE PREFERRED EMBODIMENTS

Figure 1:
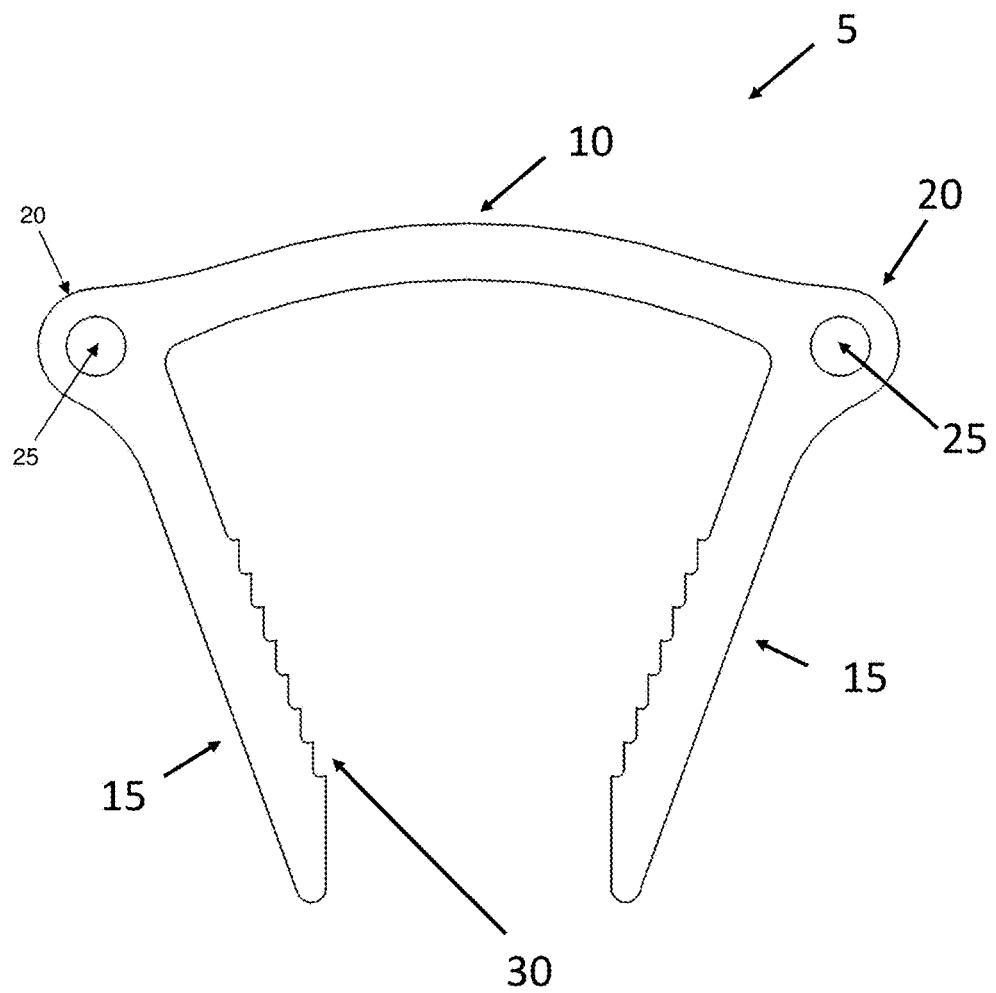
FIG. 1 is a schematic view of a novel staple formed in accordance with the present invention, wherein the staple comprises a bridge which is capable of being elastically bent and legs which are capable of being elastically pivoted about elastic hinge regions, and further wherein the staple is shown in its unstrained condition.

Novel Staple Comprising Bridge with Two Elastic Hinge Regions Incorporating Mounting Holes Looking first at FIG. 1, there is shown a novel staple 5 which is able to bring bone fragments into close proximity with each other, generate a compressive load across the fracture line, and maintain a compressive load across the fracture line while healing occurs. Staple 5 can be fully seated against the bone fragments without needing to be tamped after being released from the delivery device.

Novel staple 5 is preferably manufactured from a shape memory material (e.g., a material capable of exhibiting superelasticity and/or a temperature-induced shape change). The shape memory material may comprise a metal alloy (e.g., Nitinol) or a polymer (e.g., appropriately processed PEEK). Alternatively, staple 5 may be manufactured from another suitable material, e.g., stainless steel, titanium, etc. Staple 5 is designed to reduce fractures and generate and maintain compression between bone fragments (e.g., across a fracture line) so as to aid in fracture healing. Staple 5 comprises an elastic bridge 10 and two elastic legs 15. Bridge 10 and legs 15 meet at a pair of curved hinge regions 20 which are also elastic. Hinge regions 20 have holes 25 passing therethrough. Holes 25 may be round or may have other configurations consistent with the present invention. Legs 15 may have barbed teeth 30 to help the legs of the staple grip the bone after implantation into the bone and prevent the legs of the staple from working their way back out of the bone. In its unrestrained state, bridge 10 is bowed upwardly in the manner shown in FIG. 1. In the unrestrained state, legs 15 of staple 5 are elastically pivoted inwardly at elastic hinge regions 20 with an angle of less than 90° (relative to bridge 10). By way of example but not limitation, in one preferred form of the invention, legs 15 extend at an angle of about 65° to the longitudinal axis of bridge 10 when in their unrestrained state.

Figure 2:
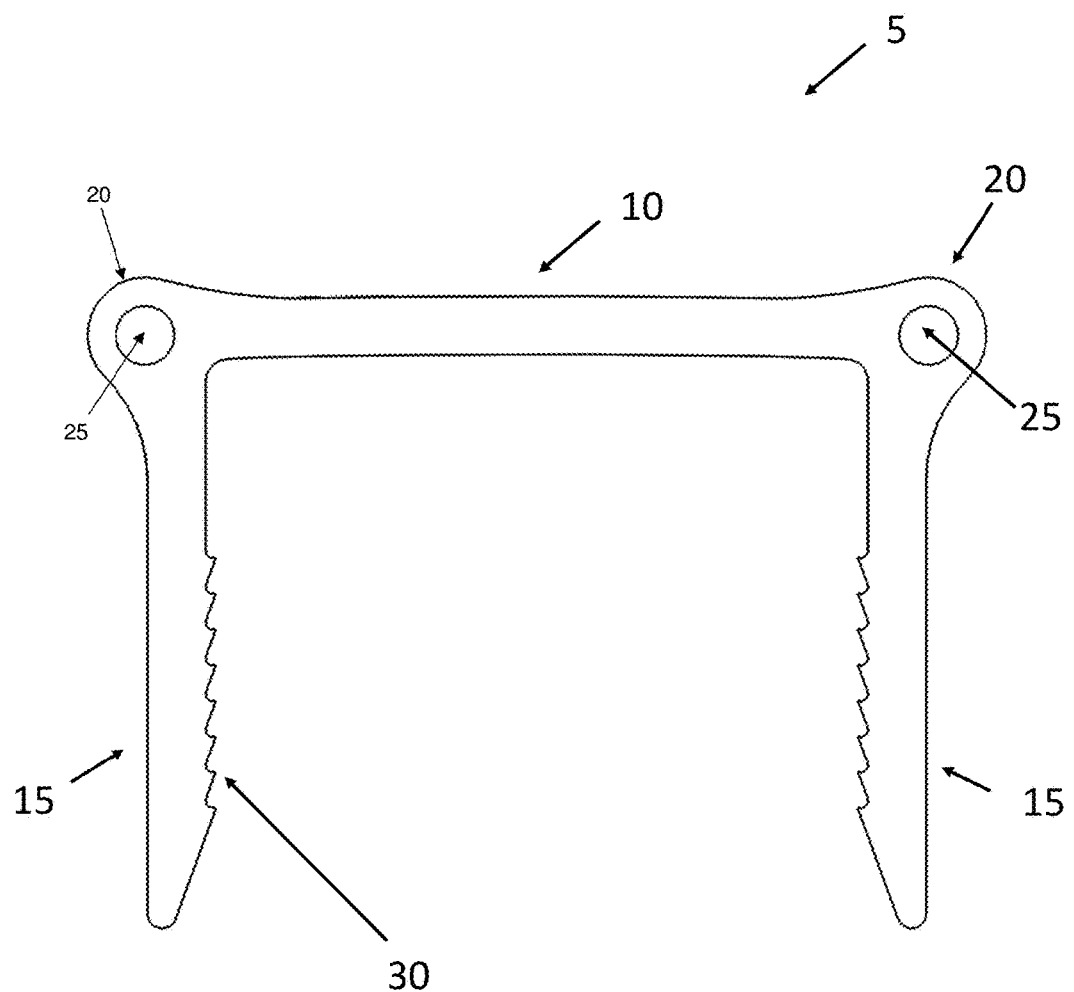
FIG. 2 is a schematic view of the novel staple shown in FIG. 1, wherein the bridge of the staple has been elastically bent (i.e., made to be more linear) and the legs of the staple have been elastically pivoted outwards (e.g., by bending at the elastic hinge regions) so as to be perpendicular to the bridge.

Prior to implantation, bridge 10 of staple 5 can be reversibly bent (i.e., bent to nearly linear) and legs 15 of staple 5 can be reversibly pivoted at elastic hinge regions 20 (e.g., by bending at the elastic hinge regions 20) to a position substantially perpendicular to bridge 10 (FIG. 2) so as to allow for insertion of the legs of the staple into a prepared fracture site, with the bridge of the staple spanning across the fracture line (see below). Note that where staple 5 is formed out of Nitinol, elastic deformations of up to approximately 8% are achievable. A delivery device (see below) can be used to elastically bend bridge 10 and pivot legs 15 at elastic hinge regions 20 (e.g., by bending at the elastic regions 20), constrain and hold the staple in its strained state prior to implantation, and then insert the staple into the prepared fracture site.

Figure 3:
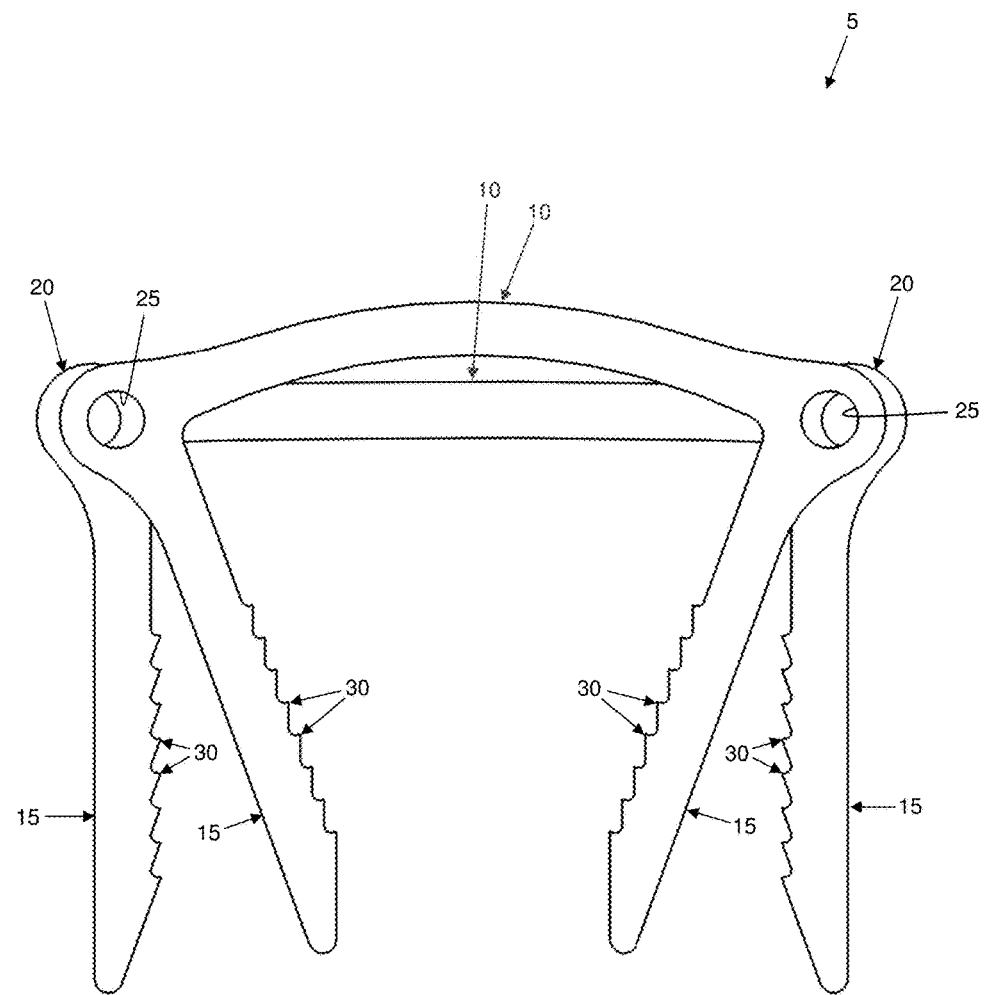
FIG. 3 is a schematic view showing how the elastically bent staple of FIG. 2 will have its legs "kick inward" when the strain on the staple is removed.
Figure 4:
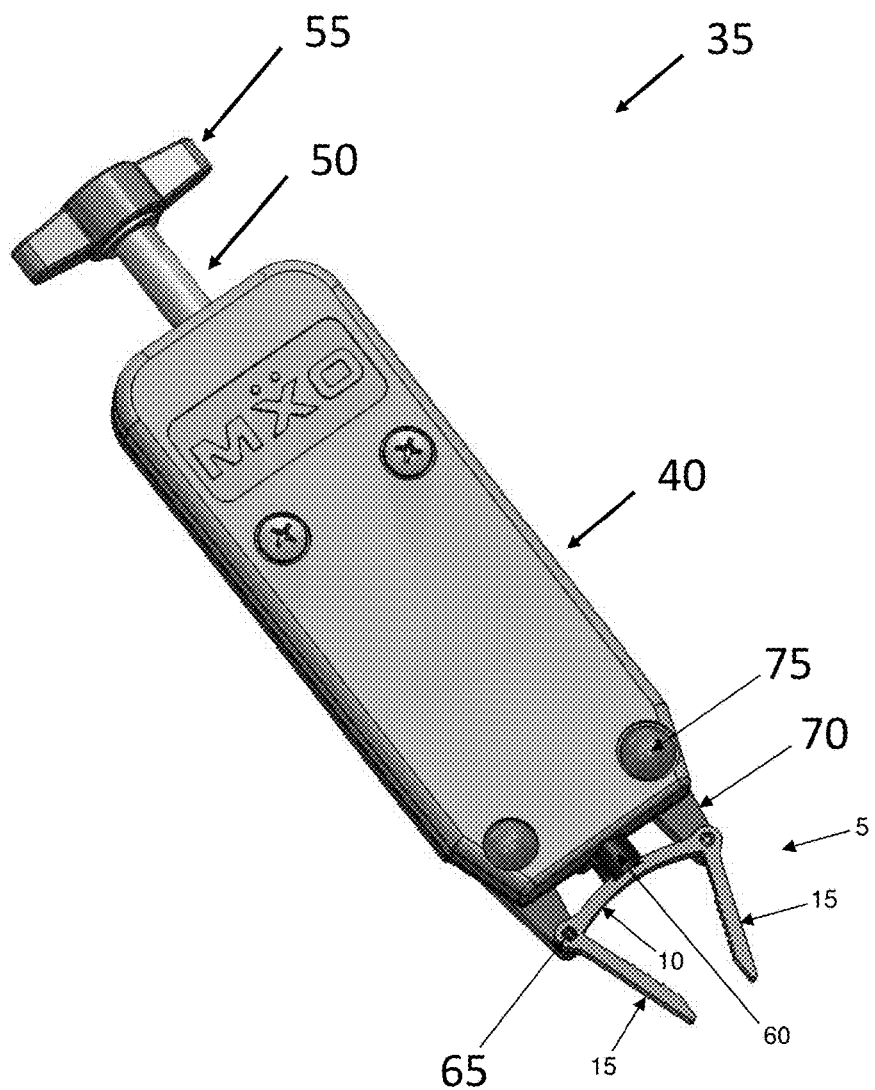
FIGS. 4, 4A, 4B, 5, 6, 6A and 6B are schematic views showing a novel delivery device which may be used with the novel staple shown in FIG. 1 to strain and constrain the staple (e.g., with the staple legs perpendicular to the staple bridge)
Figure 4A:
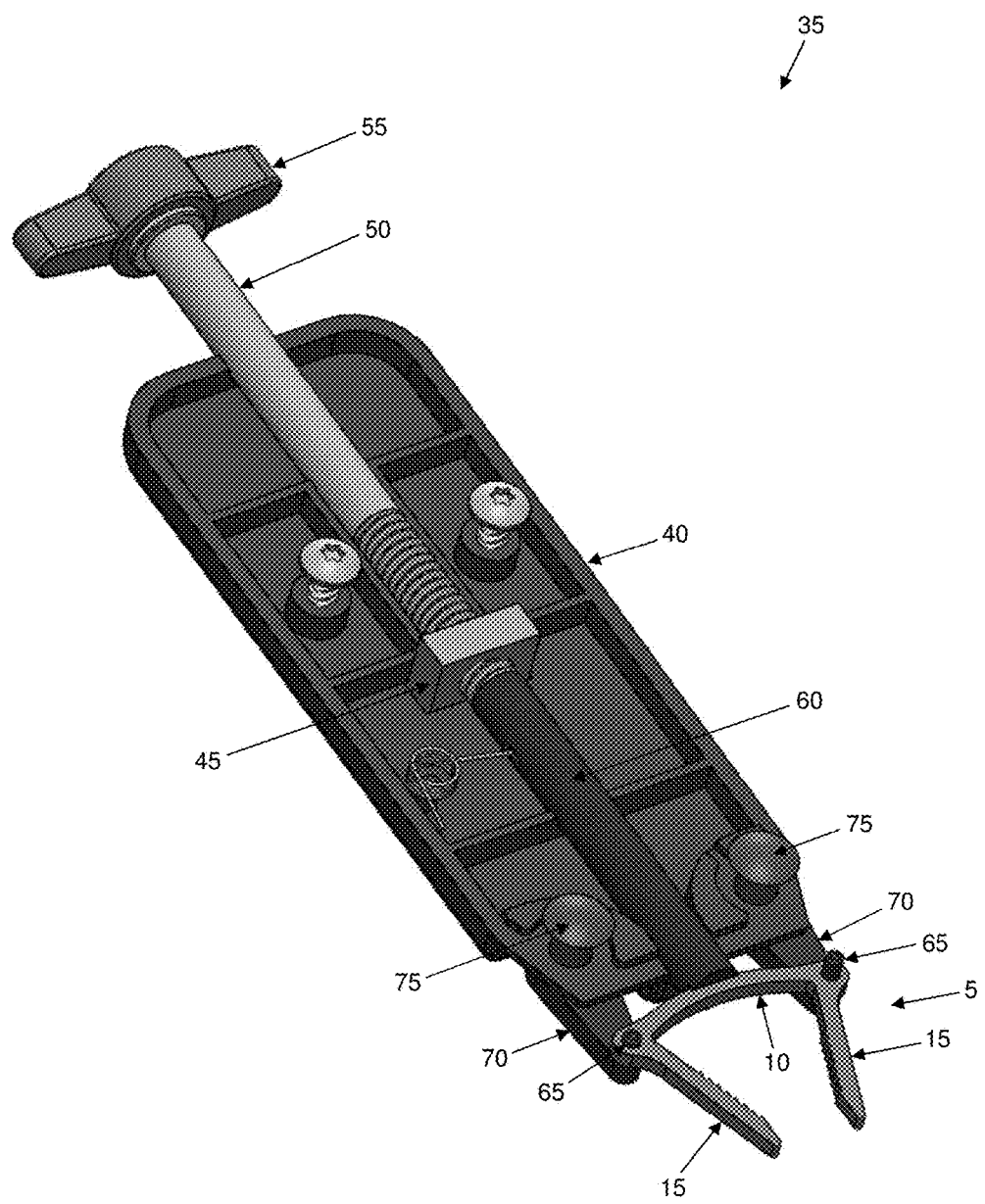
Figure 4B:
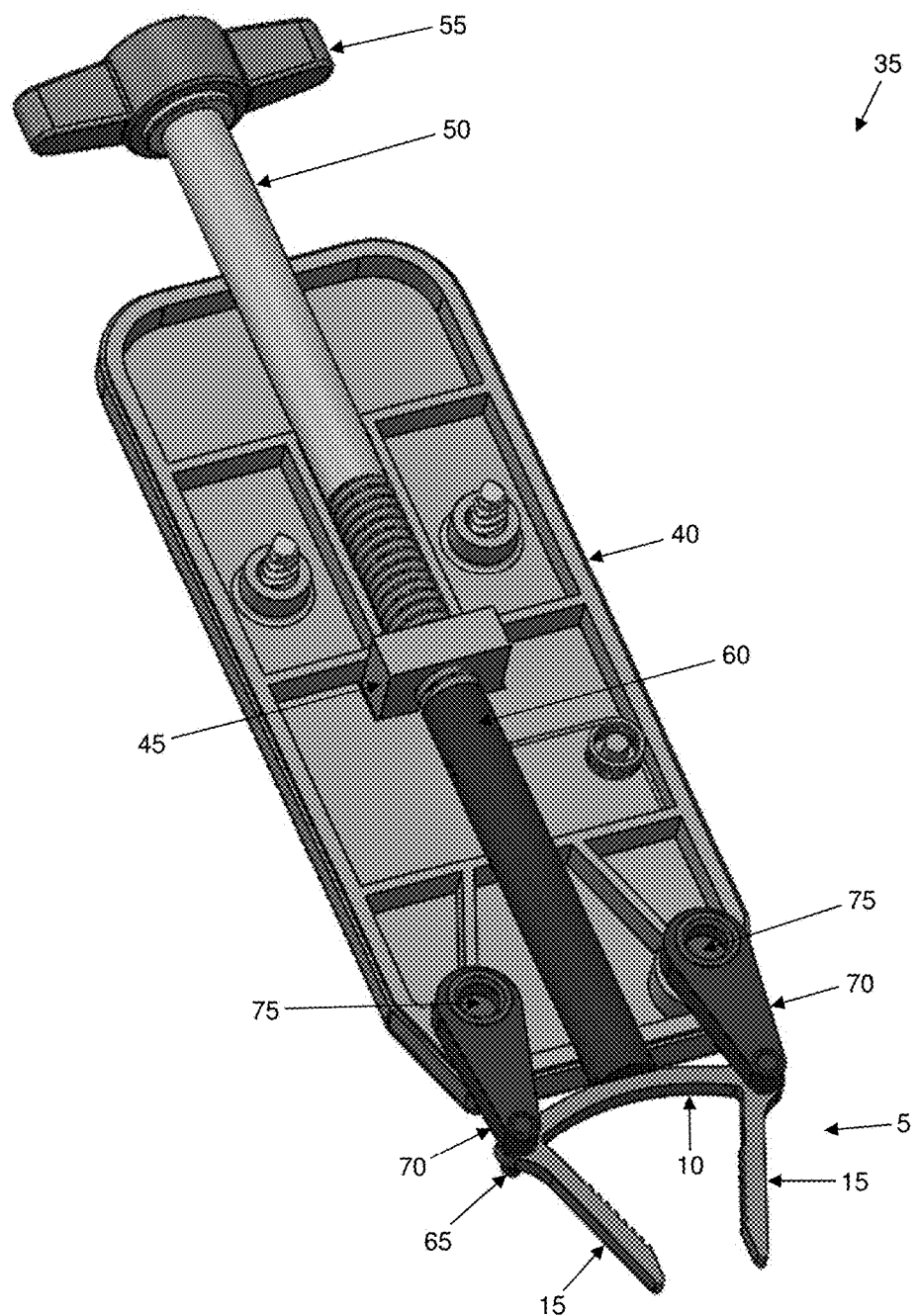
Figure 5:
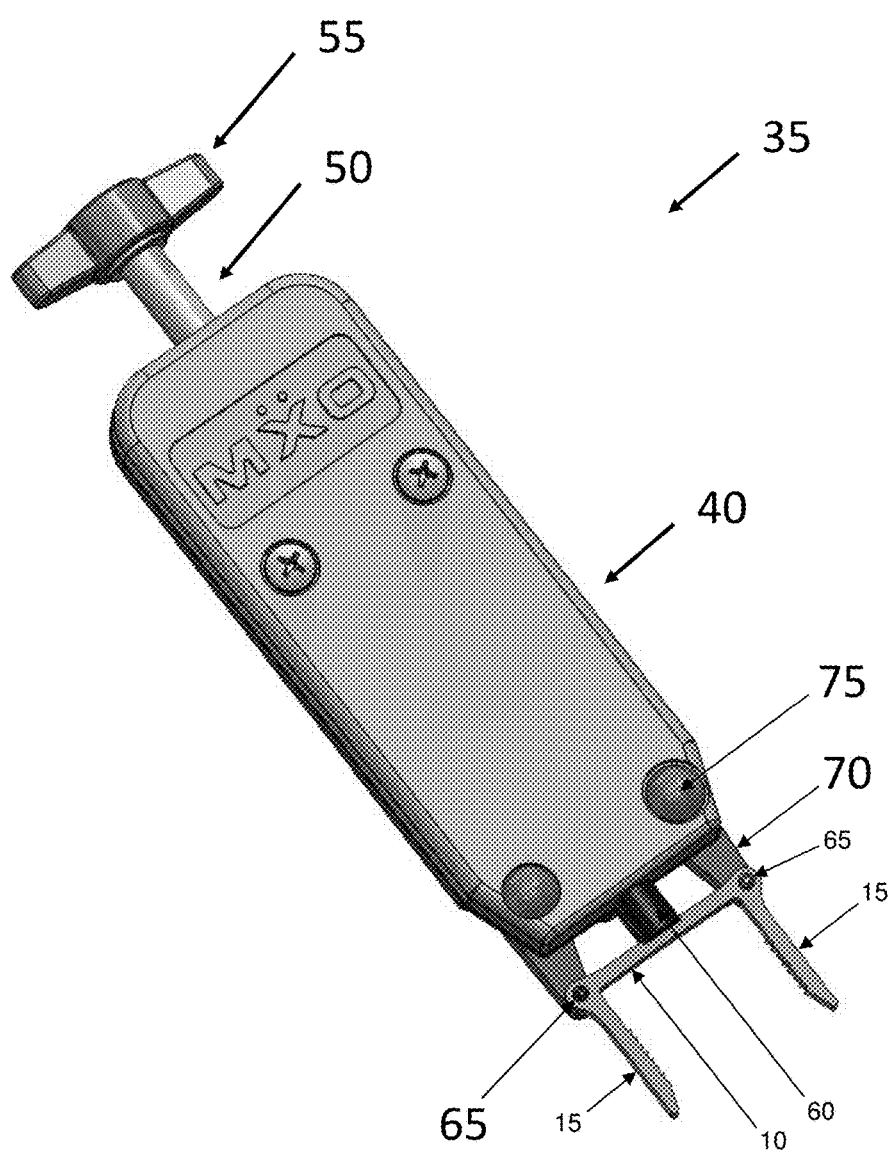
Figure 6:
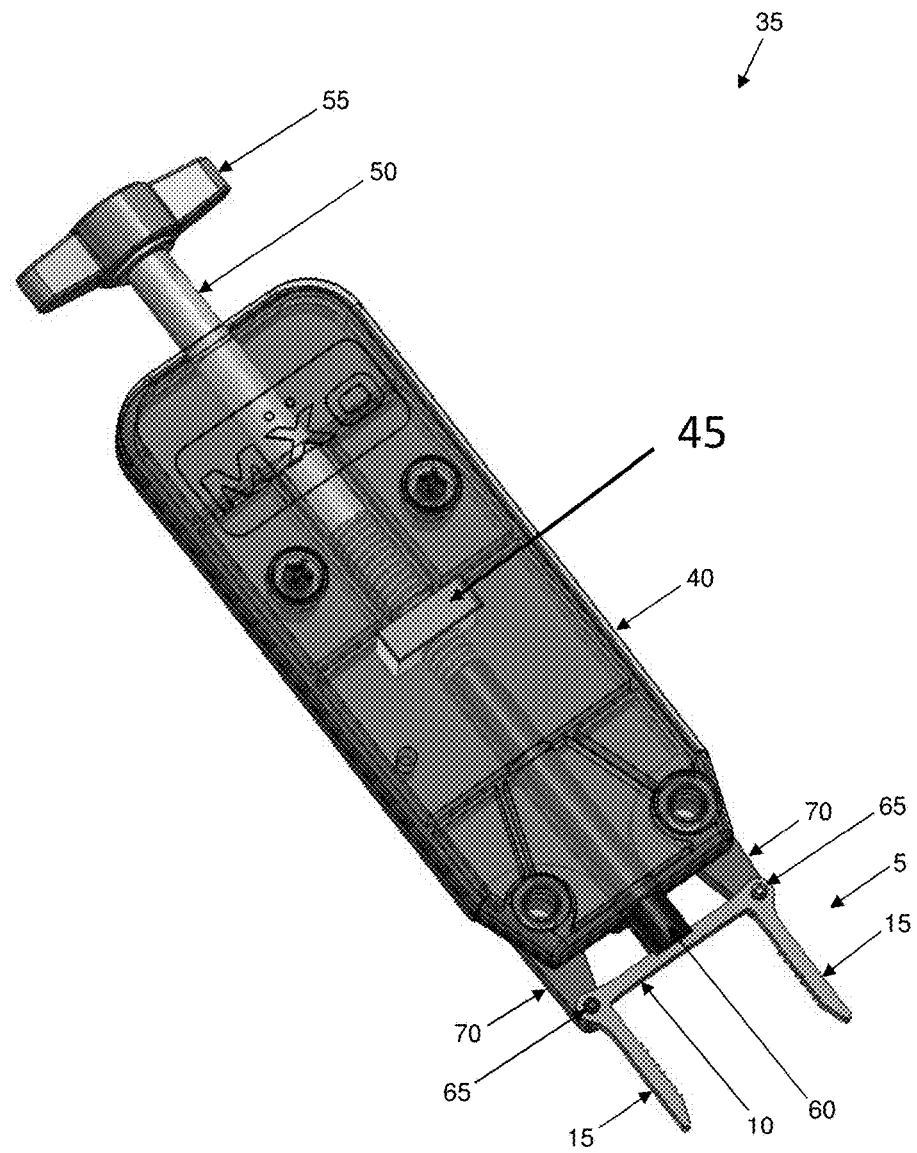
Figure 6A:
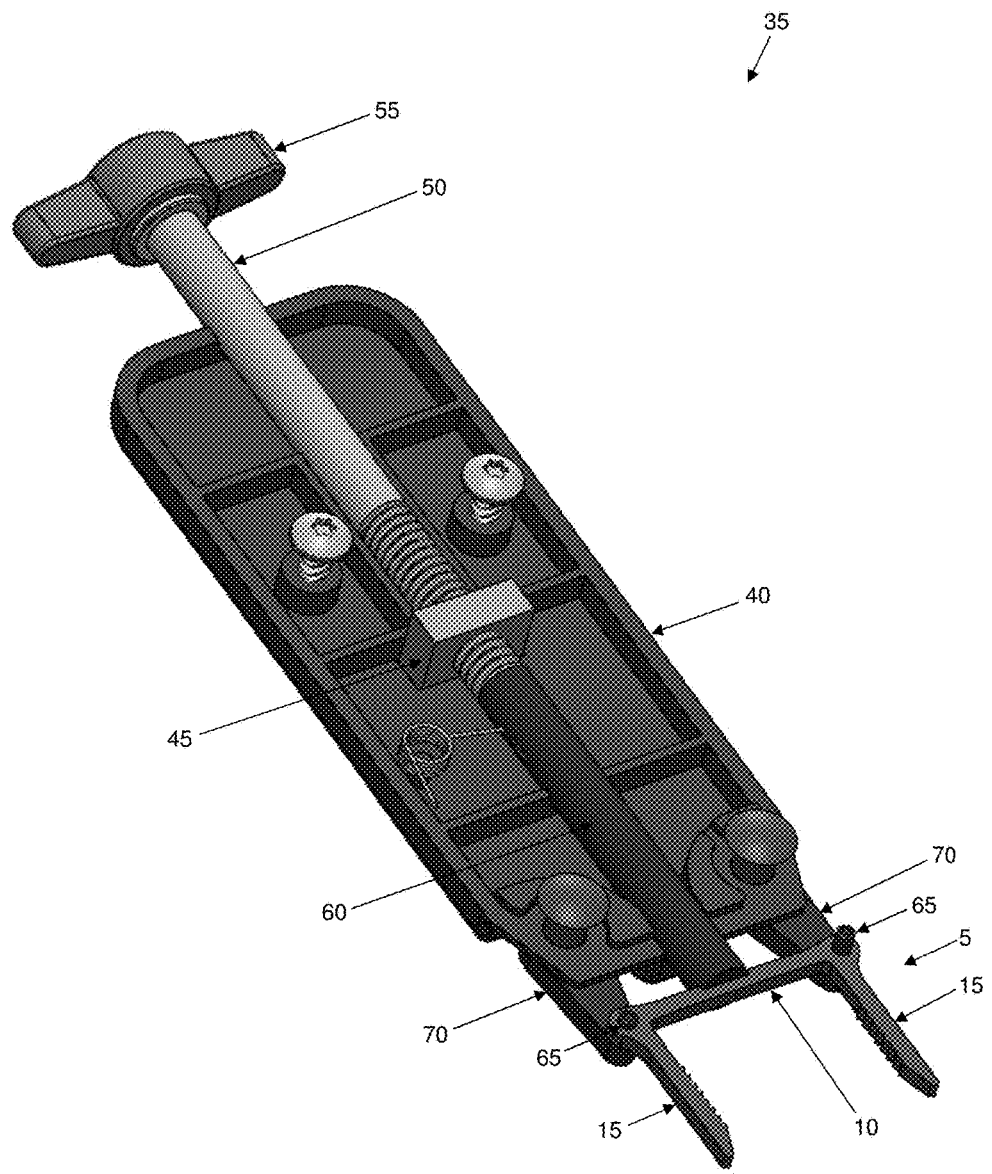
Figure 6B:
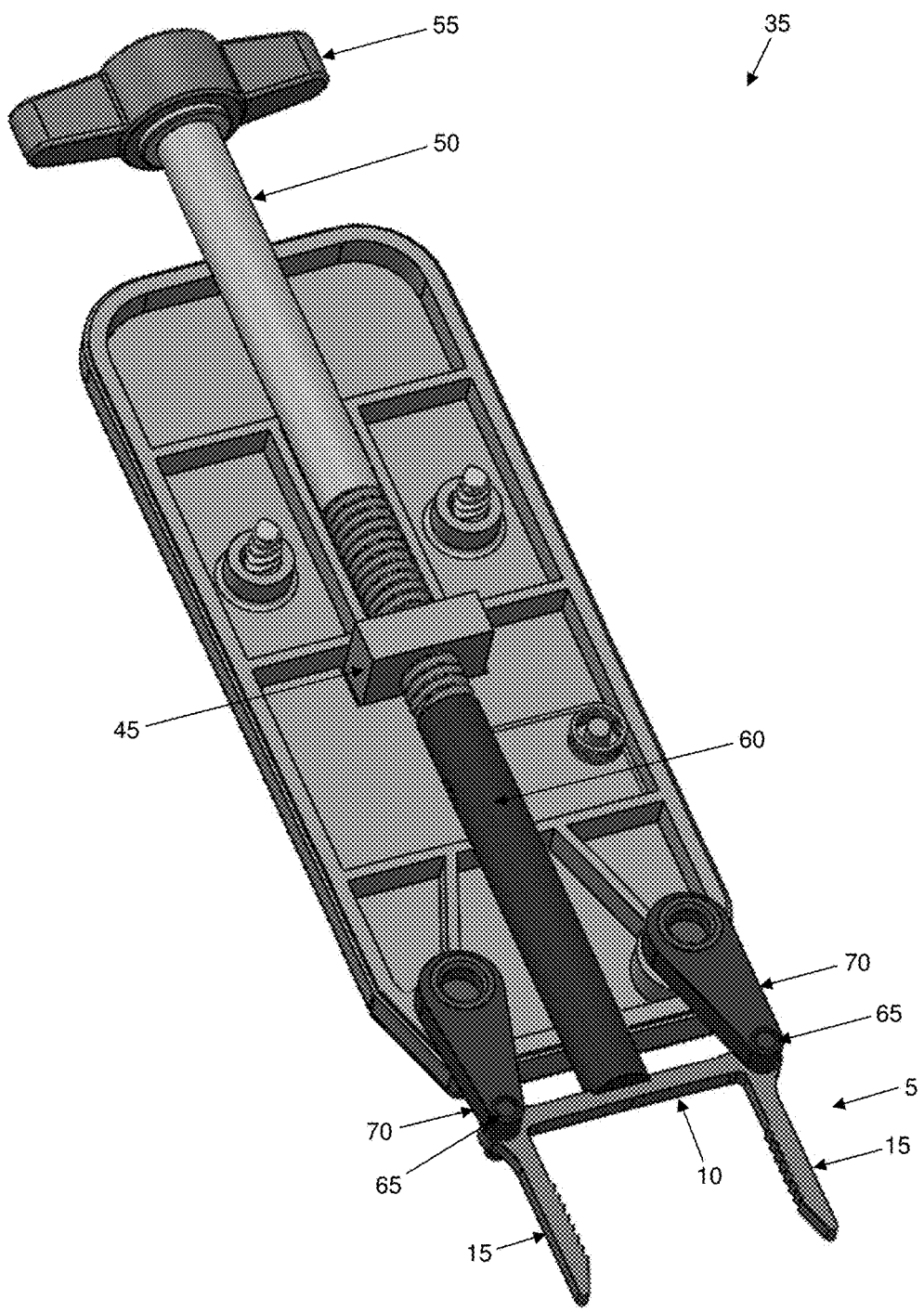

Upon insertion of the strained staple 5 into the prepared fracture site, the constraint on bridge 10 and legs 15 is removed, whereupon staple 5 attempts to return to its original un-restrained state (FIG. 3), thereby generating a compressive load across the fracture line and maintaining that compressive load across the fracture line while healing occurs.

Looking next at FIGS. 4, 4A, 4B, 5, 6, 6A, 6B, 7 and 8, there is shown a novel delivery device 35 which may be used to selectively bend bridge 10 and to selectively pivot legs 15 of staple 5 at elastic hinge regions 20 (e.g., by bending at the elastic hinge regions 20). Delivery device 35 comprises a body 40 having an internal threaded region 45 (FIG. 6) configured to mate with threaded screw 50. Threaded screw 50 has a handle 55 mounted to its proximal end. Advancing threaded screw 50 into body 40 (e.g., by selectively rotating handle 55 so as to selectively rotate threaded screw 50 such that the threads of threaded screw 50 engage internal threaded region 45) causes the distal end of threaded screw 50 to push against the proximal end of a plunger 60. The distal end of plunger 60 engages elastic bridge 10 of staple 5. When plunger 60 is moved distally (i.e., by moving threaded screw 50 distally by rotating handle 55), the distal end of plunger 60 engages elastic bridge 10 of stable 5 and elastically bends elastic bridge 10 into a more linear configuration. Staple 5 is releasably mounted to delivery device 35 by a pair of pins 65 which are mounted to two arms 70 which are each pivotally mounted to body 40 of delivery device 35 by a pivot pin 75. Pins 65 are received within holes 25 formed in staple 5. When plunger 60 is moved distally against elastic bridge 10 of staple 5, the deforming (i.e., straightening) bridge 10 of staple 5 causes arms 70 of delivery device 35 to pivot outwardly, with elastic hinge regions 20 of staple 5 bending about pins 65 so as to pivot staple legs 15 outwardly.

Figure 7:
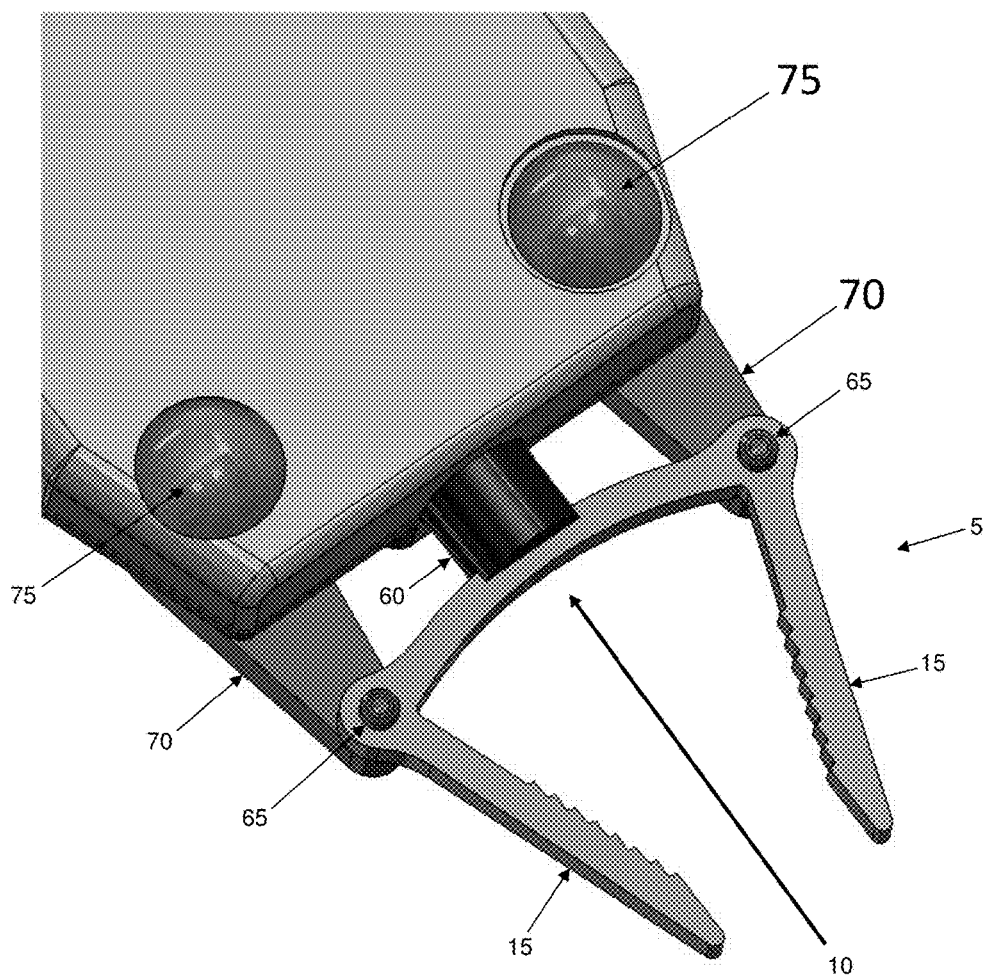
FIGS. 7 and 8 are schematic views showing the delivery device of FIGS. 4, 4A, 4B, 5, 6, 6A and 6B being used with the novel staple shown in FIG. 1 to elastically bend the bridge of the staple and elastically pivot the legs of the staple (e.g., by bending at the elastic hinge regions)
Figure 8:
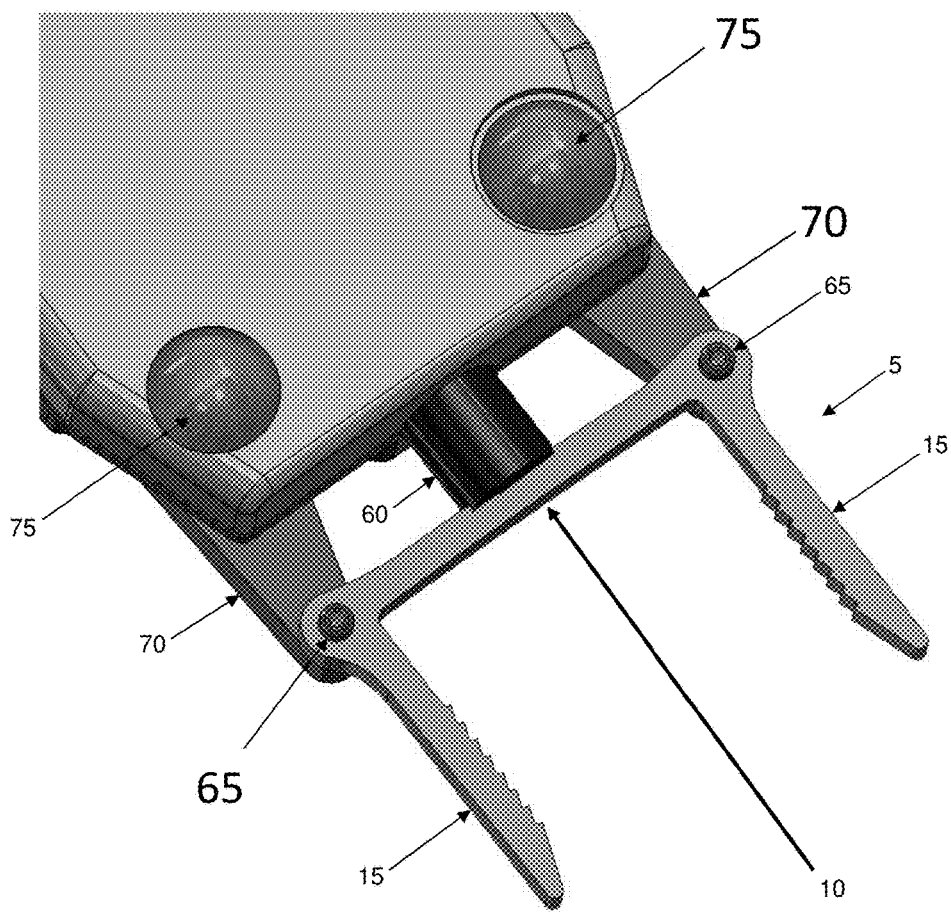

More particularly, and looking now at FIGS. 7 and 8, when staple 5 is mounted to pins 65 of delivery device 35 (i.e., with pins 65 being received within holes 25 of staple 5) and handle 55 is rotated so as to advance threaded screw 50 distally, plunger 60 is also advanced distally, whereby to push against elastic bridge 10, causing elastic bridge 10 to bend and become more linear, and causing arms 70 of delivery device 35 to articulate (i.e., pivot) outwardly. As this occurs, elastic hinge regions 20 of staple 5 bend about pins 65, causing elastic legs 15 to be pivoted about elastic hinge regions 20 so as to be oriented generally perpendicular to elastic bridge 10 (FIG. 8).

Note that staple 5 is configured so that the force that is generated as staple 5 reconfigures (i.e., as bridge 10 and legs 15 attempt to return back to their original disposition) is less than the "tear through" force of the bone receiving legs 15, i.e., staple 5 is specifically engineered so as to not "tear through" the bone tissue when staple 5 attempts to return to its original, unbiased shape. The compressive forces generated by staple 5 as staple 5 attempts to reconfigure (i.e., as bridge 10 contracts and as elastic legs 15 of staple 5 attempt to pivot inboard toward one another about elastic hinge regions 20) can be controlled by modulating the material properties of staple 5 and/or the geometry of staple 5.

By way of example but not limitation, the percentage of cold work in the shape memory material forming staple 5 affects the compressive force that is generated by the reconfiguring staple 5. As the percentage of cold work increases, the compression force that is generated decreases. In one preferred form of the present invention, staple 5 has between about 15% and about 55% cold work in order to control the recovery force (i.e., the compressive force generated by bridge 10 and legs 15 as staple 5 reconfigures) of staple 5; however, if desired, other degrees of cold work may be used, and/or the material comprising staple 5 may not be cold worked at all.

By way of further example but not limitation, another material property that affects the compression force generated by staple 5 as the staple reconfigures is the temperature differential between the body that staple 5 will be implanted into (assumed to be approximately 37° C., which is the temperature of a human body) and the austenite finish temperature of the shape memory material forming staple 5. A smaller temperature differential between the two will result in staple 5 generating a smaller compressive load as staple 5 reconfigures; conversely, a larger temperature differential between the two will result in staple 5 generating a larger compressive load as staple 5 reconfigures. The shape memory material that staple 5 is made out of should, preferably, have an austenite finish temperature of greater than about −10° C., resulting in a temperature differential of about 47° C. when the staple is implanted (assuming that the staple is implanted in a human body).

By way of further example but not limitation, staple geometry also affects the compression forces generated as staple 5 reconfigures. More particularly, the cross-sectional areas of elastic bridge 10, elastic hinges 20 and elastic legs 15 affect the compression forces generated by the reconfiguring staple 5. As the cross-sectional areas increase, the compression forces that the reconfiguring staple 5 generates also increase.

Elastic legs 15 of staple 5 are critical for transmitting the compression force to the bone without "tearing through" the bone. The height, width, and length of the staple legs, and the geometry of the staple legs, are all significant factors relating to the staple's ability to not "tear through" the bone. Elastic legs 15 having greater surface area are better able to distribute the compression force and thus resist "tearing through" the bone.

Figure 9:
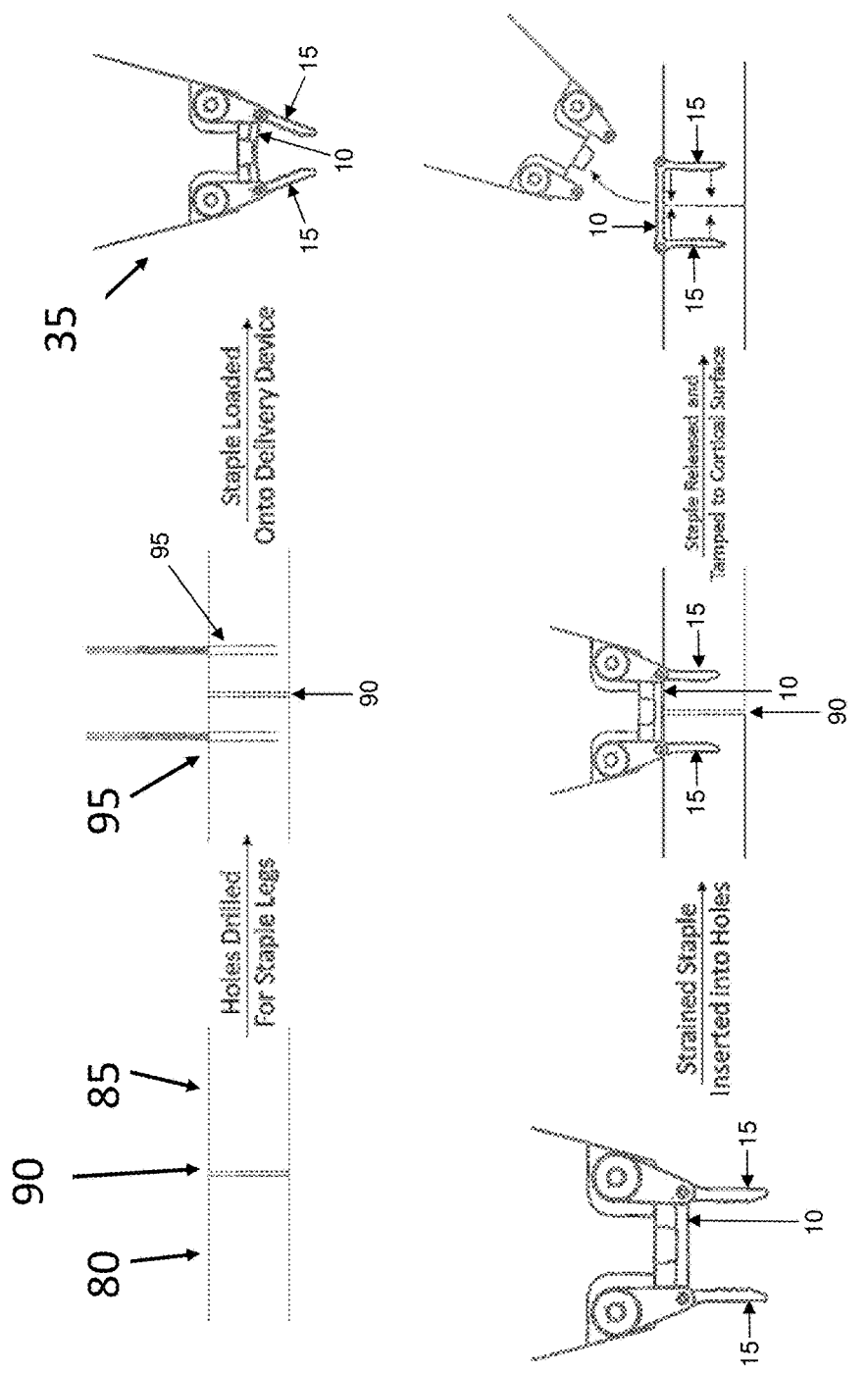
FIGS. 9 and 10 are schematic views showing how the novel staple of FIG. 1 may be used to generate and maintain compression between bone fragments so as to aid in fracture healing.

FIG. 9 shows how staple 5 may be used to reduce a fracture and generate and maintain compression between bone fragments 80 and 85.

More particularly, the fracture 90 which is to be fused is first re-approximated and reduced. A drill guide (not shown) of the sort well known in the art is used to drill two holes 95 the correct distance apart to accommodate the legs 15 of staple 5. Staple 5 is mounted to pins 65 of delivery device 35, and delivery device 35 is used to bend bridge 10 and straighten legs 15 of staple 5 in the manner discussed above (i.e., by turning handle 55 to advance plunger 60 which is used to bend bridge 10 and pivot legs 15 at elastic hinge regions 20). While still mounted to pins 65 of delivery device 35, legs 15 of staple 5 are placed into the pre-drilled holes 95. Staple 5 is then released from pins 65 of delivery device 35, i.e., by turning handle 55 in the opposite (e.g., counter-clockwise) direction and sliding staple 5 off of pins 65. This allows the bent bridge 10 and pivoted legs 15 of staple 5 to attempt to return (reconfigure) to their un-bent configuration, thereby applying compression across fracture 90.

Note that in the preferred form of the invention, staple 105 is designed to generate and maintain compression between both the cortical bone and the cancellous bone of the bone fragments so as to promote effective healing. In this respect note also that, while bridge 10, elastic hinges 20 and the proximal (i.e., bridge-side) portions of legs 15 typically engage cortical bone, the pivoting nature of the reconfiguring distal portions of legs 15 will help apply enhanced compressive forces to the cancellous bone (i.e., the interior bone) of the bone fragments.

Figure 10:
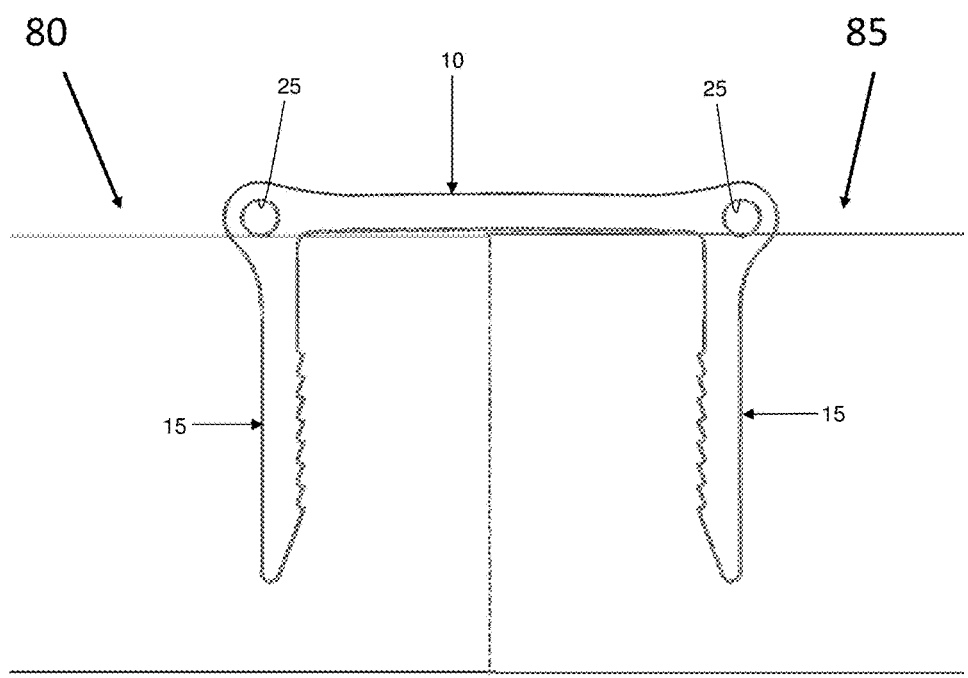
Figure 11:
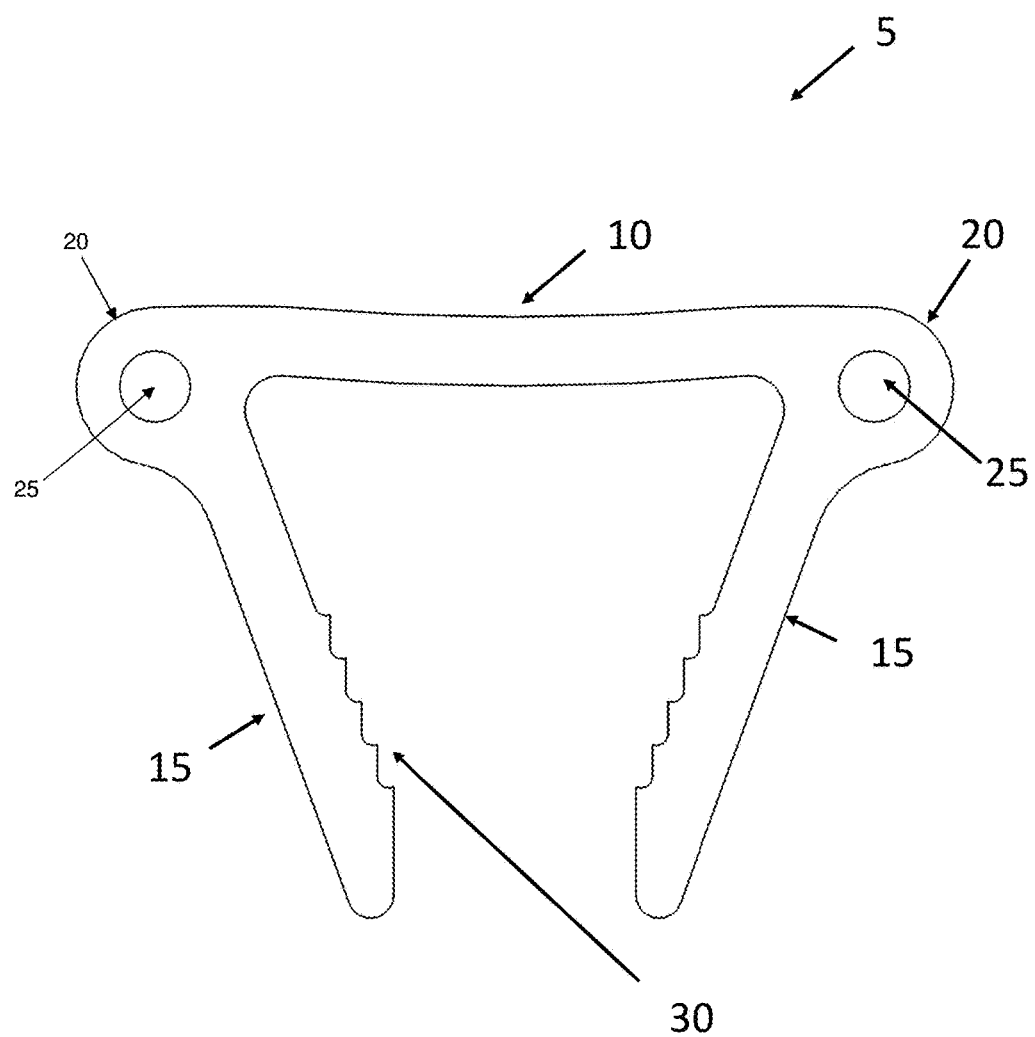
FIGS. 11-13 are schematic views showing another novel staple formed in accordance with the present invention, wherein the novel staple comprises a bridge which is capable of being elastically bent and legs which are capable of being elastically pivoted about elastic hinge regions—the novel staple of FIGS. 11-13 has a concave bridge specifically engineered to match the anatomy of the fracture site (e.g., an Akin Osteotomy site), where

Significantly, it should be appreciated that since staple 5 is mounted to delivery device 35 via pins 65 being inserted into holes 25, staple 5 can be fully inserted into pre-drilled holes 95 with bridge 10 in direct contact with bone fragments 80 and 85. Tamping is not needed in order to fully seat staple 5 (FIG. 10).

It should also be appreciated that, if desired, staple 5 can be used to attach soft tissue to bone (e.g., to attach a rotator cuff to bone).

In some circumstances it can be desirable to modify delivery device 35 so as to ensure that legs 15 cannot be pivoted at hinge regions 20 beyond 90 degrees (relative to the longitudinal axis of bridge 10) when legs 15 of staple 5 are pivoted outboard. In other circumstances, it may be desirable for delivery device 35 to allow legs 15 of staple 5 to be pivoted outboard less than, or greater than, 90 degrees to allow insertion into slightly mispositioned (or angled) drill holes 95.

It should be appreciated that following implantation, if desired, delivery device 35 can also be used to remove staple 5 from the bone. More particularly, delivery device 35 can be used to re-engage staple 5 at the holes 25 (i.e., by inserting pins 65 of delivery device 35 into holes 25 of staple 5) in the hinge regions 20 of staple 5. Turning handle 55 (e.g., clockwise) causes plunger 60 to bend staple bridge 10 and to reconfigure staple 5 such that bridge 10 is substantially perpendicular to staple legs 15. Staple 5 can then be removed from the bone by pulling the staple out perpendicular to the bone.

Additionally, staple delivery device 35 allows the surgeon to "sense" how much compression staple 5 will exert on the bone when it is released from delivery device 35 and attempts to reconfigure. More particularly, as the surgeon turns handle 55 to straighten bridge 10 and open staple legs 15 (e.g., by turning handle 55 clockwise), handle 55 requires greater levels of torque as staple 5 is opened (i.e., as bridge 10 is pushed down and legs 15 are pivoted outboard), thereby providing a degree of tactile feedback to the surgeon. The torque that the surgeon applies to handle 55 is proportional to the compression that staple 5 will exert on the bone as the staple reconfigures.

Thus delivery device 35 also allows the surgeon to ascertain and control how much compression staple 5 will exert when the staple is released from delivery device 35. The greater the degree to which bridge 10 is straightened and legs 15 of staple 5 are opened (i.e., pivoted outboard), the more compressive force staple 5 will exert on the bone when it is released from delivery device 35.

Additionally, delivery device 35 also allows the surgeon to control the rate at which staple 5 loads the bone as the staple is removed from delivery device 35. More particularly, turning handle 55 of delivery device 35 counterclockwise releases the downward (i.e., distal) force that plunger 60 exerts on bridge 10 of staple 5. This allows staple 5 to attempt to recover (i.e., reconfigure) to its original shape and apply compression across the fracture site. It may be desirable to allow the surgeon to be able to control this "release rate" so that the bone is not damaged as staple 5 reconfigures and so that staple 5 remains in the desired location.

In one preferred form of the invention, staple 5 and delivery device 35 are provided in the form of a sterilized kit. Staple 5 may be "pre-loaded" (i.e., mounted) onto delivery device 35 (i.e., with pins 65 of delivery device 35 extending through holes 25 of staple 5). Staple 5 may be mounted on delivery device 35 in an unconstrained or a constrained state. The kit may include additional instruments to aid in the implantation of the staple (e.g., k-wire, drill bit, staple size guide, etc.).

EXAMPLE

The compressive force generated by staples of the present invention formed out of Nitinol with greater than 20% cold work are able to generate 50 to 100 Newtons of force depending on the staple dimensions. This is more than twice the compression force able to be generated by conventional staples of a similar size.

Figure 12:
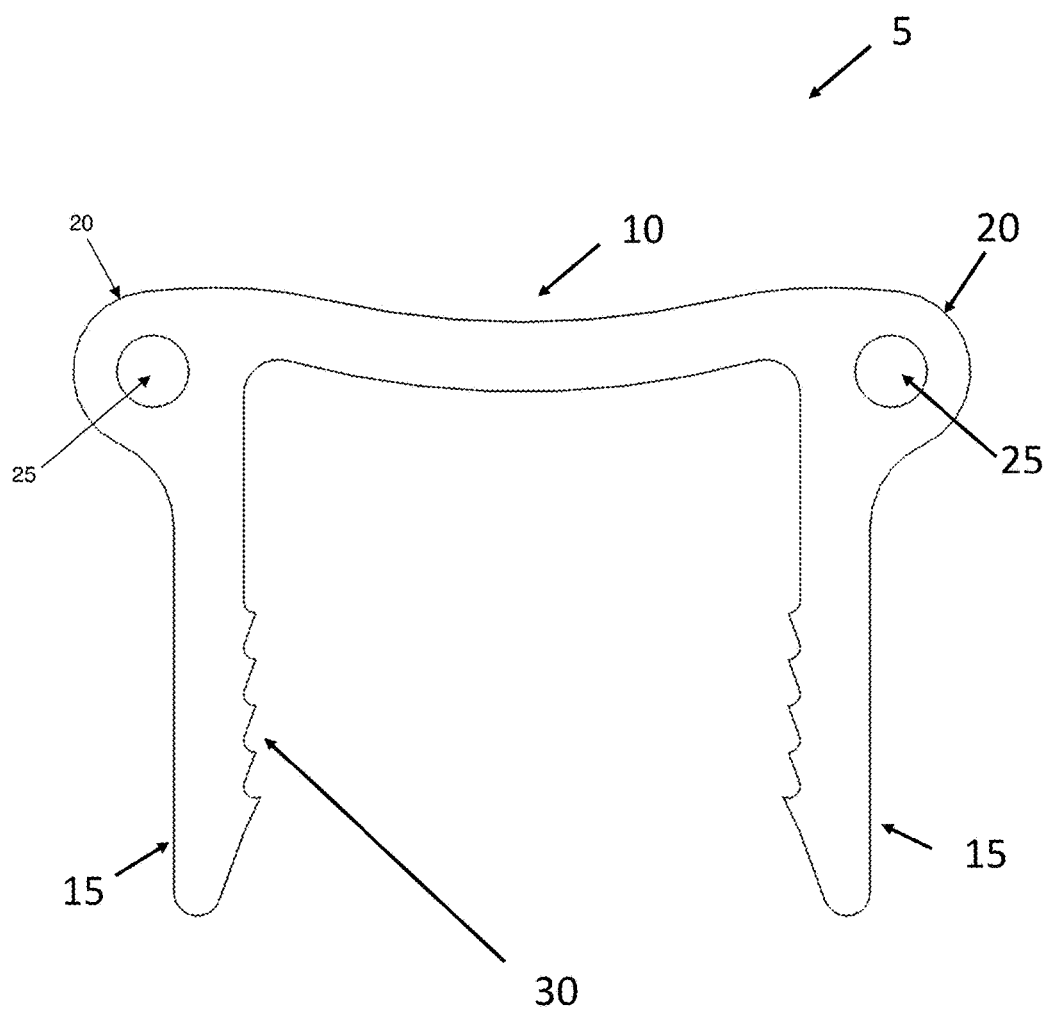
Figure 13:
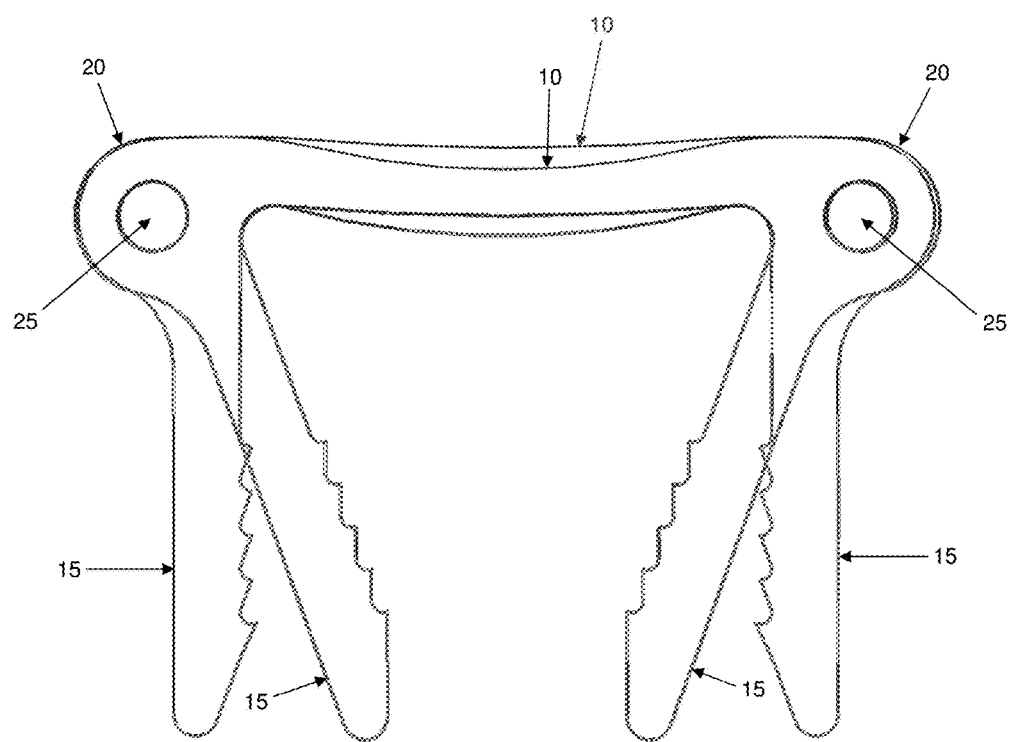

Alternative Configurations of Novel Staple Formed in Accordance with the Present Invention Looking now at FIGS. 11-19 it should be appreciated that staple bridge 10 may be formed so as to have a different configuration. By way of example but not limitation, it may be beneficial for staple bridge 10 to have a concave geometry (FIGS. 11-13), such that when bridge 10 of staple 5 is reversibly bent (i.e., so that legs 15 are pivoted so that they are parallel to each other), bridge 10 can bend downwardly, i.e., so as to become more concave (FIG. 12). Upon insertion of the strained staple 5 across the prepared fracture site, the constraint on bridge 10 and hinges 20 is removed, whereupon staple 5 attempts to return (i.e., reconfigure) to its original un-restrained state (FIG. 13), thereby generating a compressive load across the fracture line and maintaining that compressive load across the fracture line while healing occurs. By way of example but not limitation, it may be beneficial to provide a staple 5 having a concave bridge 10 for the treatment of fractures where the anatomy is "hourglass" shaped (e.g., in an Akin Osteotomy).

Figure 14:
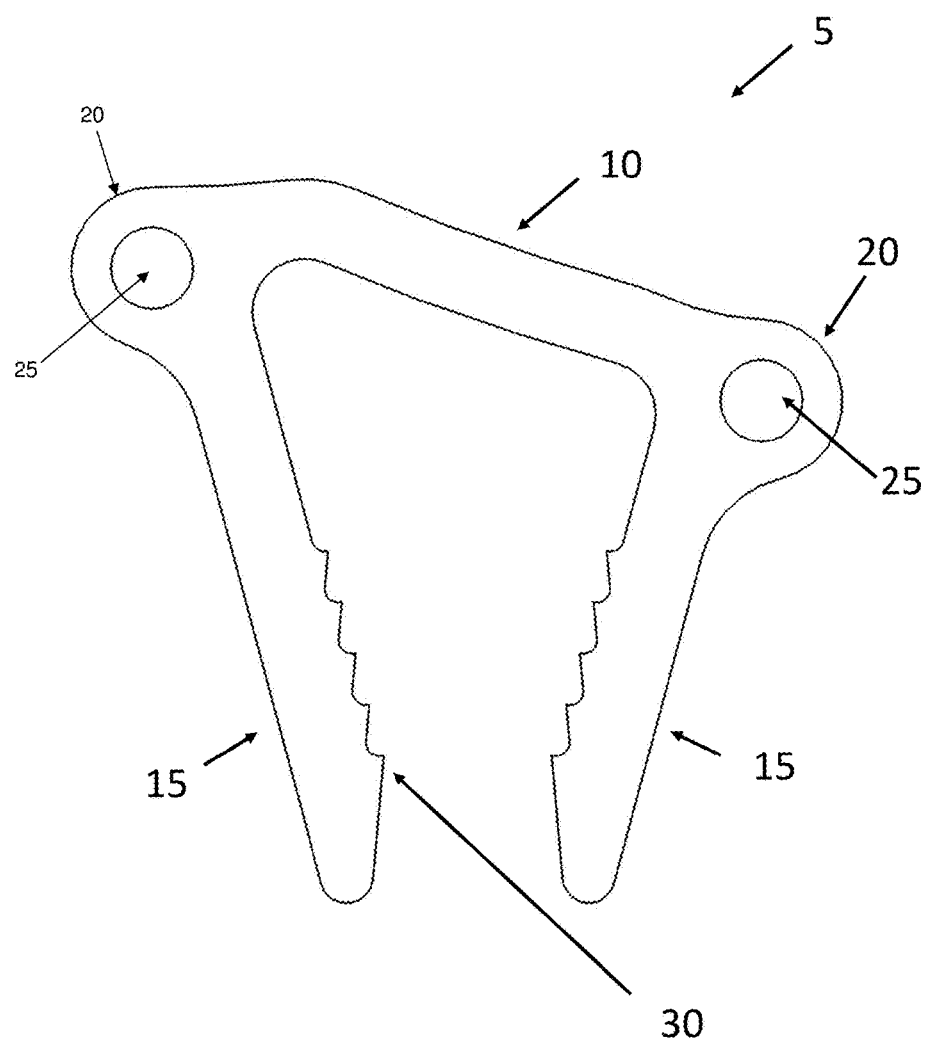
FIGS. 14-16 are schematic views showing still another novel staple formed in accordance with the present invention, wherein the novel staple comprises a sloped bridge which is capable of being elastically bent and legs which are capable of being elastically pivoted about elastic hinge regions—the novel staple of this design has a slanted bridge specifically engineered to match the anatomy of the fracture site (e.g., an Akin Osteotomy site), where
Figure 15:
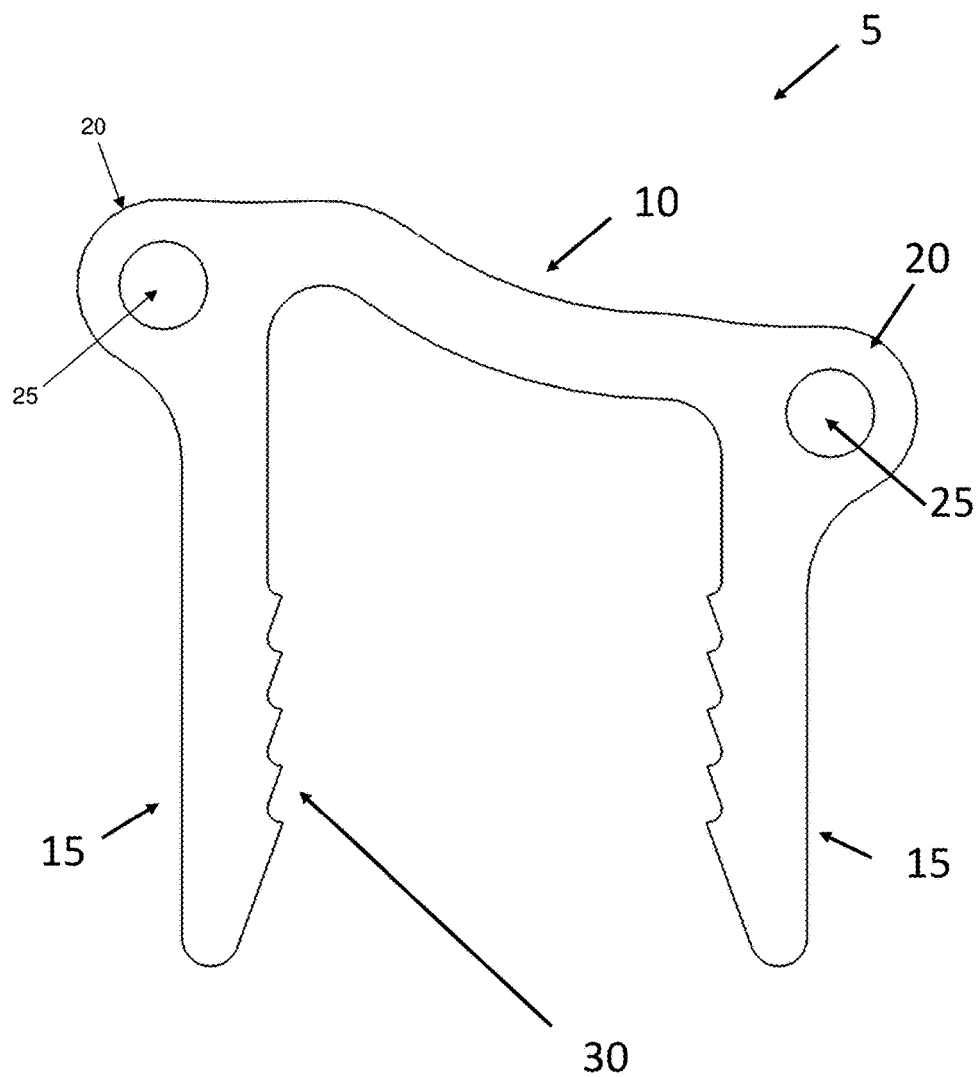
Figure 16:
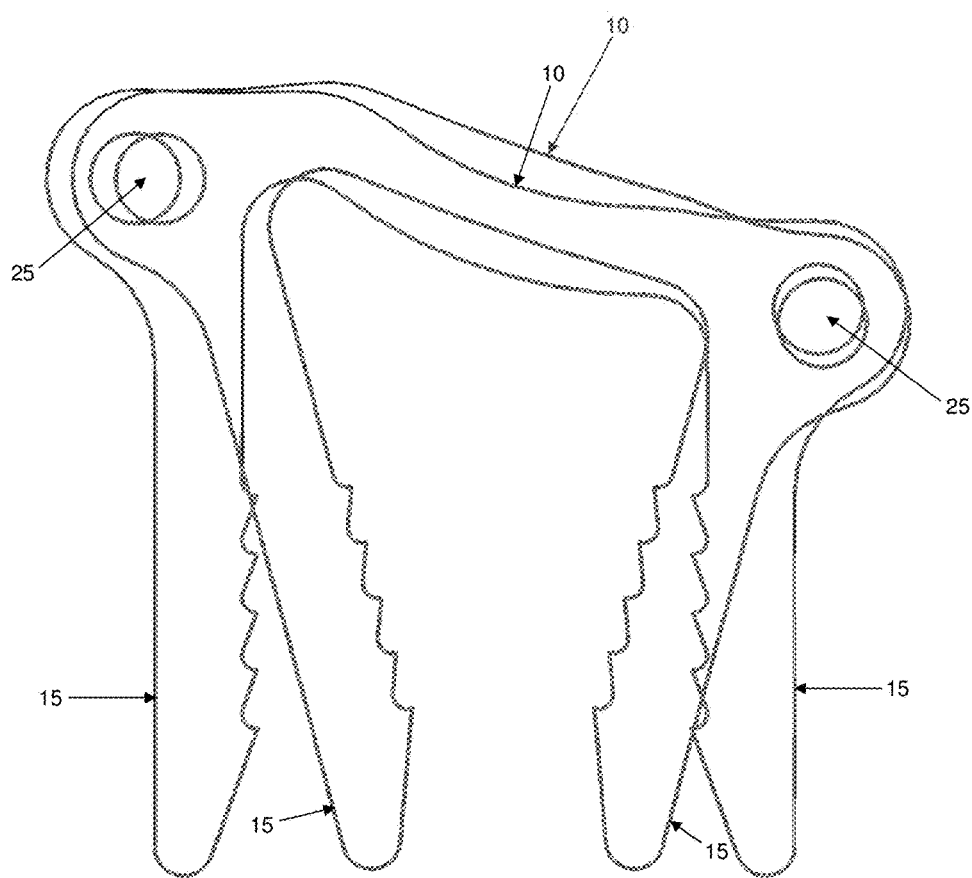

It may also be desirable to provide a staple 5 having a bridge 10 formed with a sloped geometry (FIG. 14). In this form of the invention, legs 15 can be elastically pivoted so as to be parallel to one another (FIG. 15). Upon insertion of the strained staple 5 into the prepared fracture site, the constraint on bridge 10 and hinges 20 is removed, whereupon staple 5 attempts to return to its original un-restrained state (FIG. 16), thereby generating a compressive load and maintaining that compressive load while healing occurs. It may be desirable to provide staple 5 having this configuration for the treatment of fractures where the anatomy is non-linear (e.g., at the metaphyseal flares).

Figure 17:
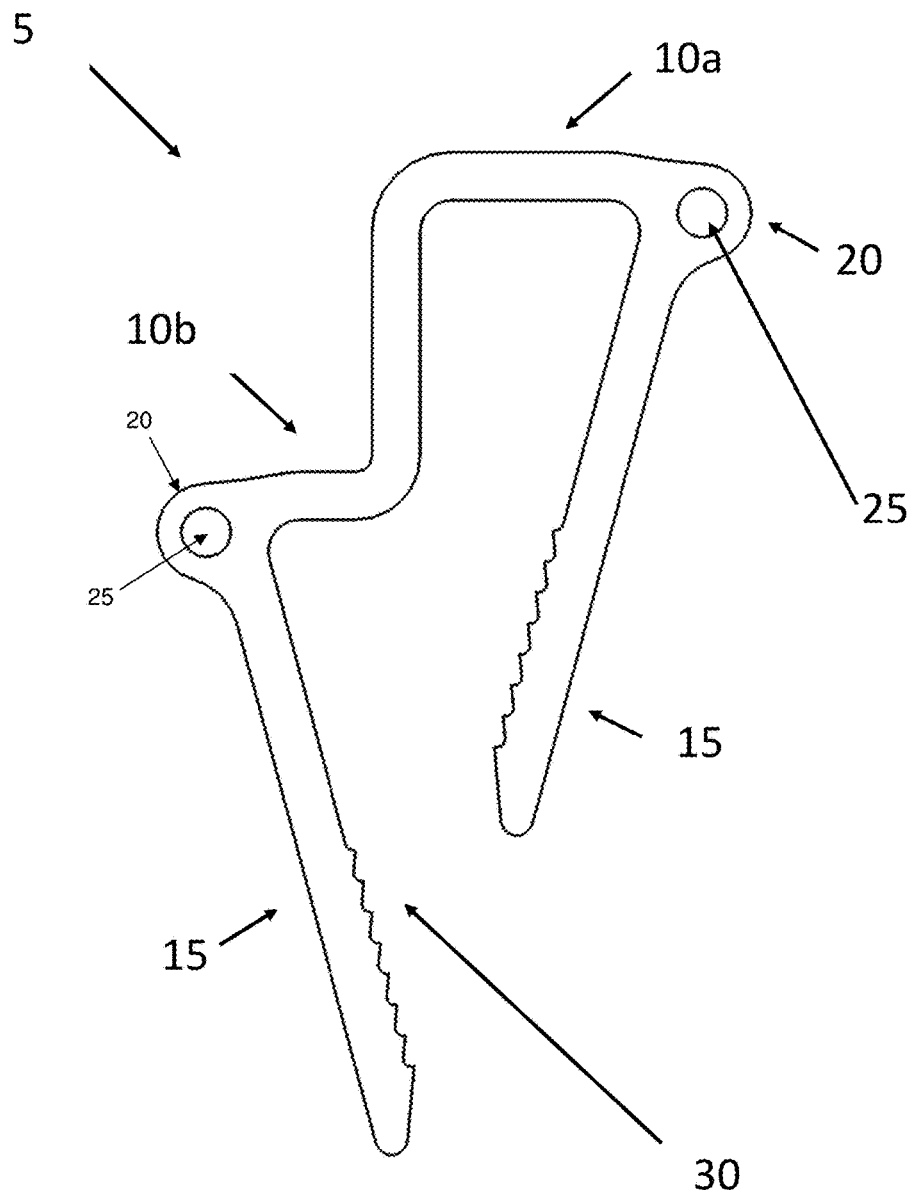
FIGS. 17-19 are schematic views showing yet another novel staple formed in accordance with the present invention, wherein the novel staple comprises a bridge which is capable of being elastically bent and legs which are capable of being elastically pivoted about elastic hinge regions—the staple of this design has a stepped bridge specifically engineered to match the anatomy of the fracture site (e.g., sliding calcaneal osteotomies, calcaneocuboid fusions, Lapidus procedures, etc.), where
Figure 18:
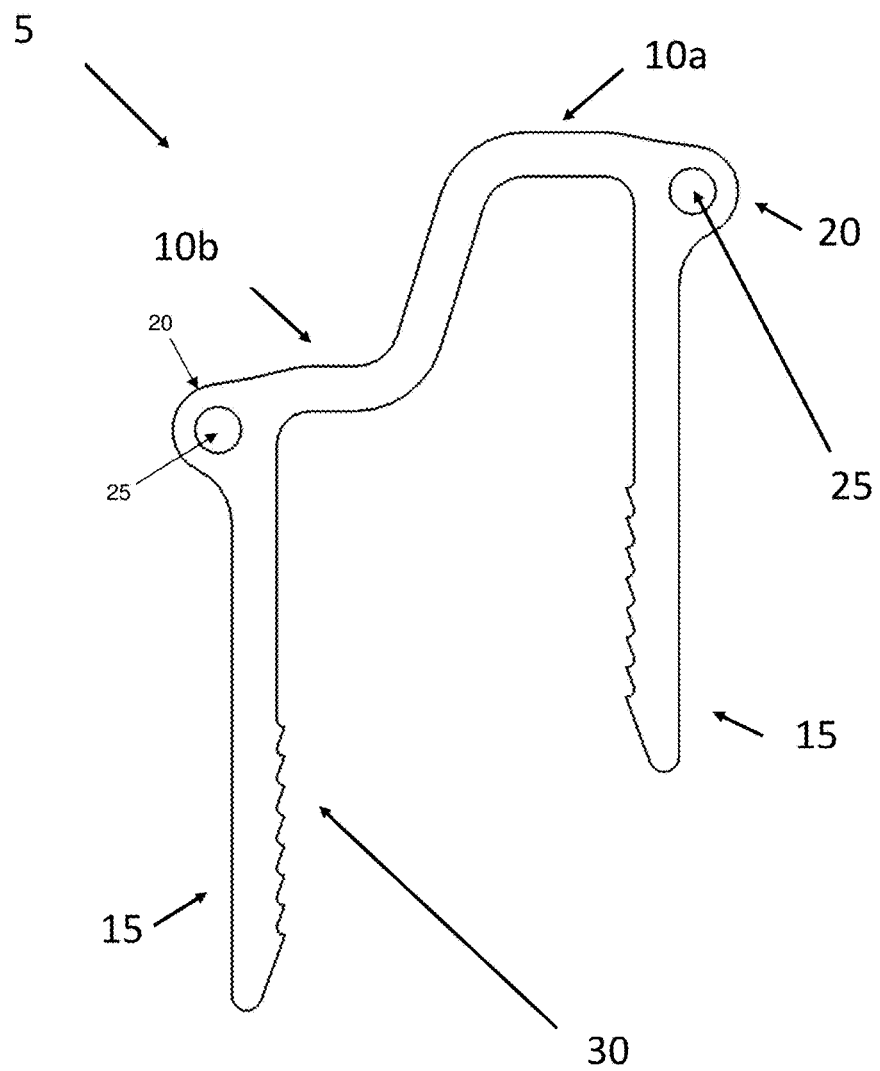
Figure 19:
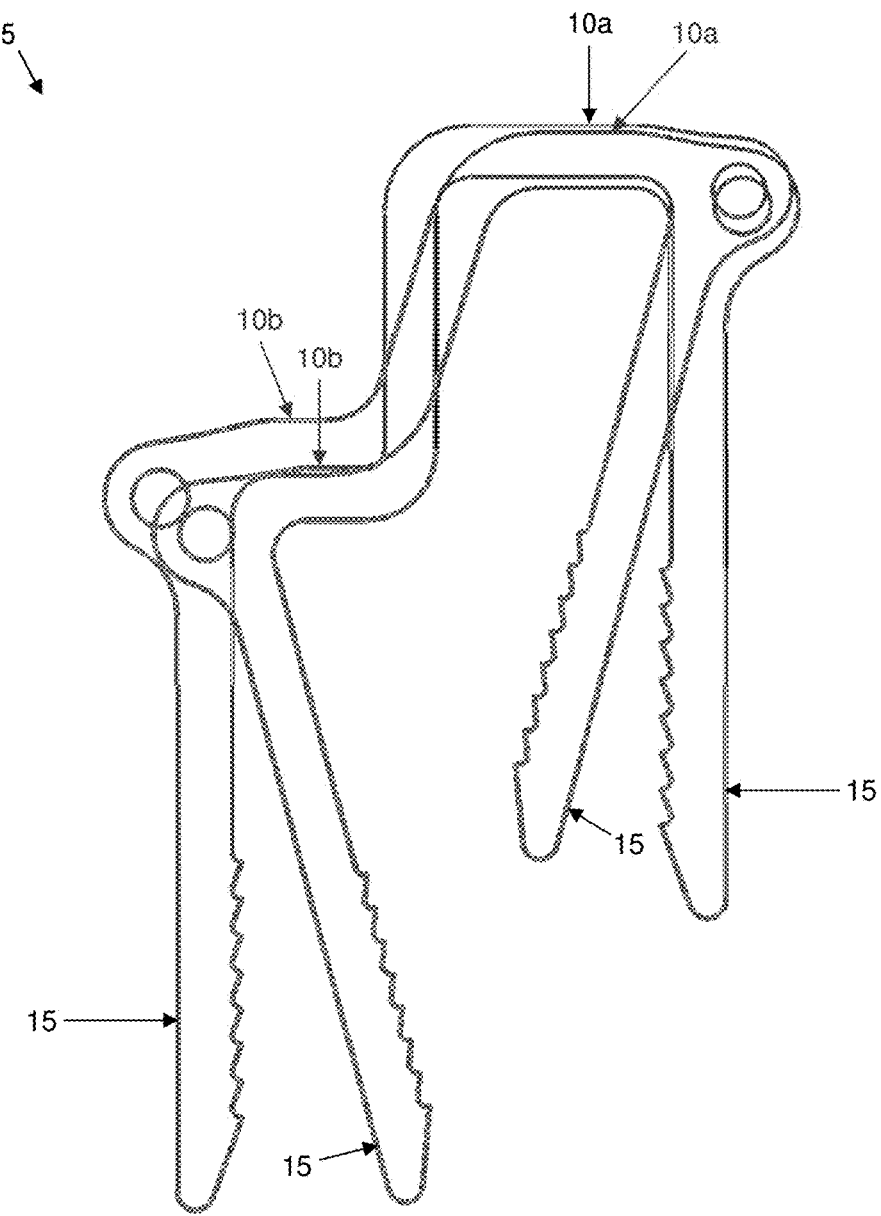

It may also be desirable to provide staple 5 with bridge 10 having a stepped geometry (FIG. 17). In this form of the invention, when staple 5 is reversibly strained (i.e., so that legs 15 are pivoted outboard so as to be parallel to each other), bridge segments 10a and 10b are parallel to each other (FIG. 18). Upon insertion of the strained staple 5 into the prepared fracture site, the constraint on bridge 10 and hinges 20 is removed, whereupon staple 5 attempts to return (i.e., reconfigure) to its original un-restrained state (FIG. 19), thereby generating a compressive load across the fracture line and maintaining that compressive load across the fracture line while healing occurs. It may be desirable to provide a staple 5 having this configuration for the treatment of fractures where the anatomy is uneven (i.e., sliding calcaneal osteotomies, calcaneocuboid fusions, Lapidus procedures, etc.).

Figure 20:
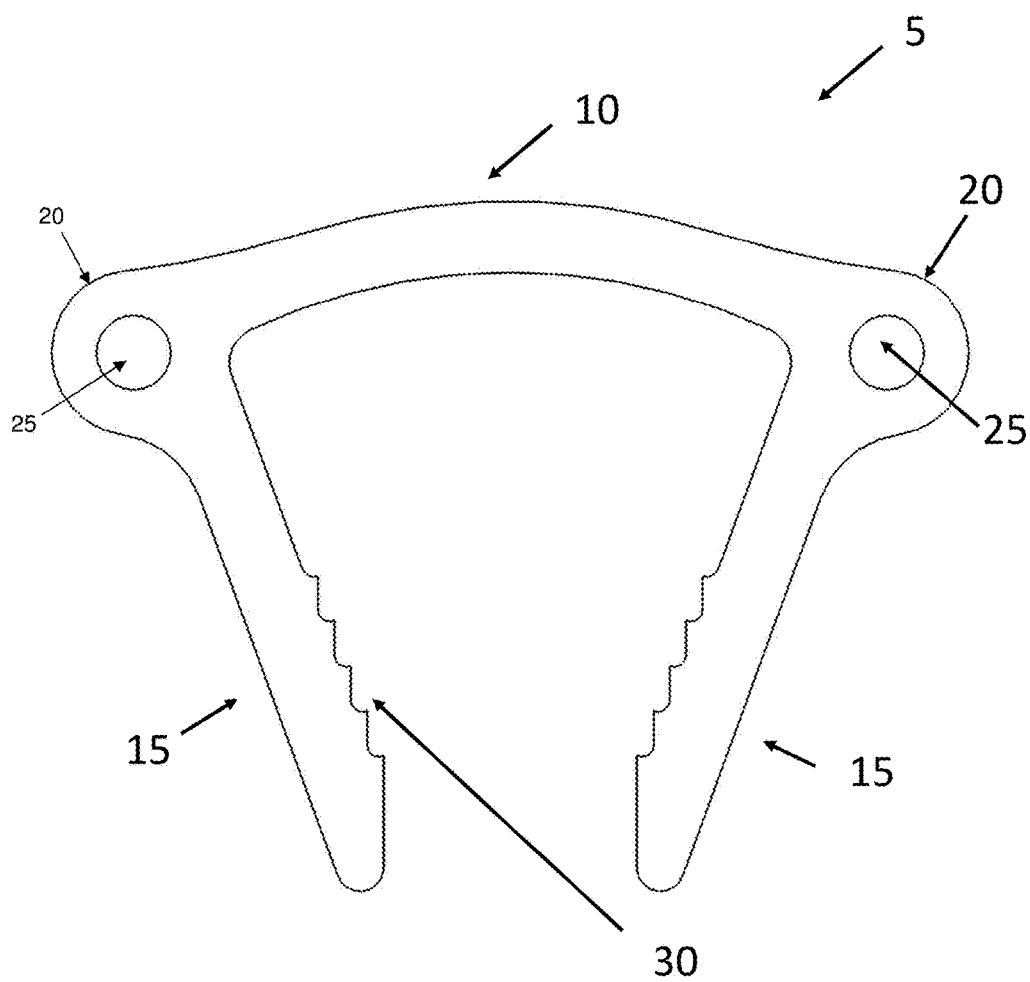
FIGS. 20-22 are schematic views showing another novel staple formed in accordance with the present invention, wherein the staple comprises a malleable bridge which is capable of being plastically bent (i.e., to take a set) and legs which are capable of being elastically pivoted about elastic hinge regions
Figure 21:
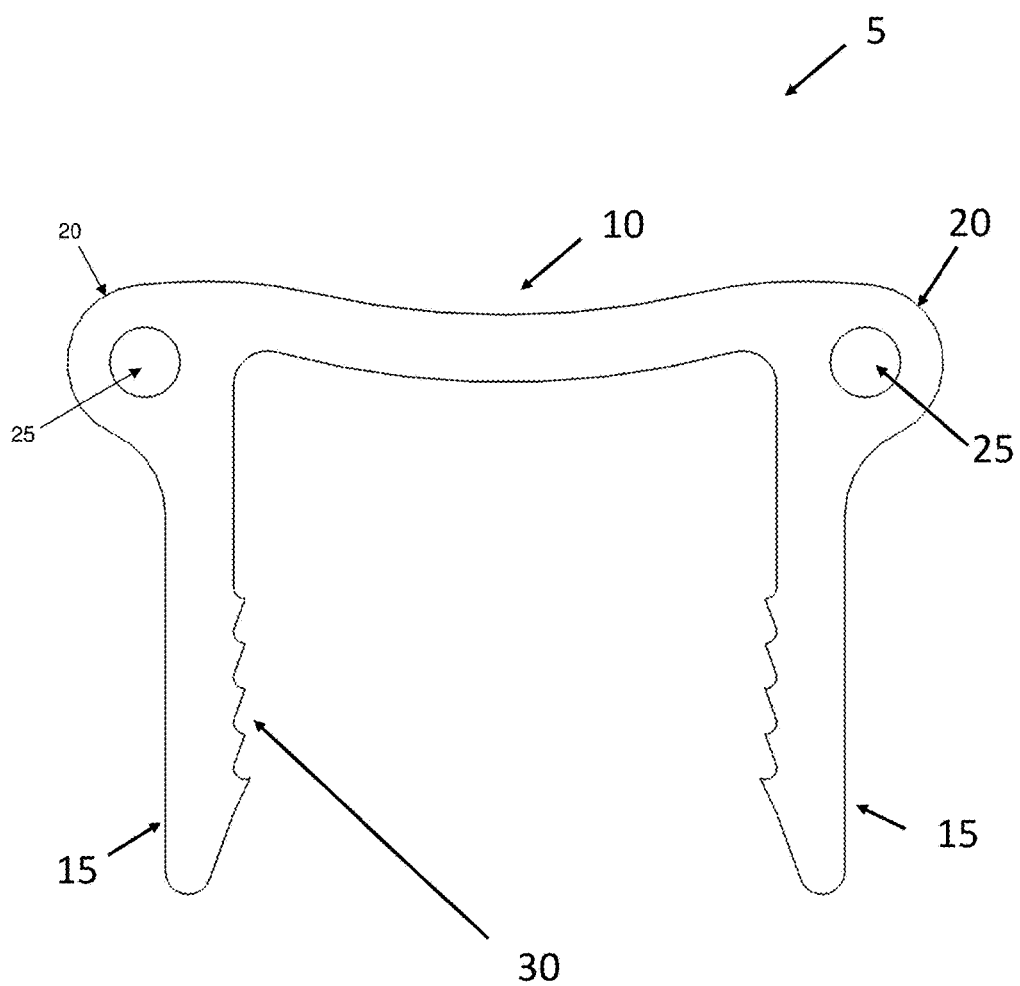
Figure 22:
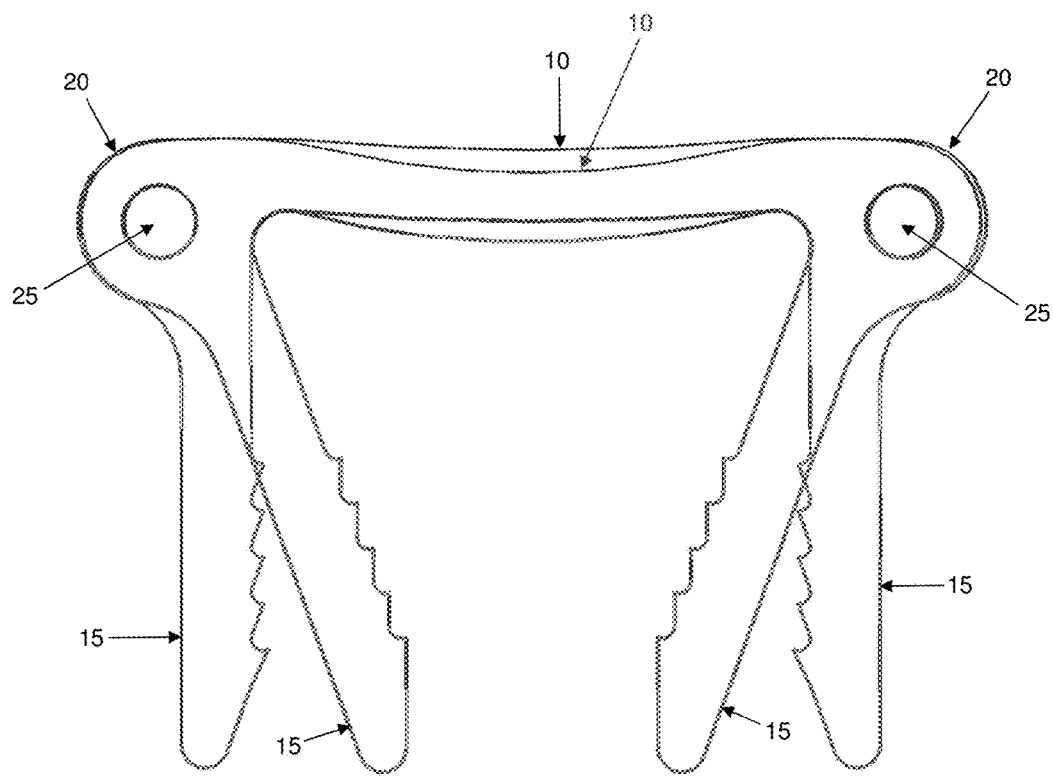

Novel Staple Having a Malleable Bridge which is Plastically Deformable to Take a Set It may also be desirable to provide a staple 5 having a malleable bridge 10 which is plastically deformable so as to be able to take a set (FIG. 20). This allows the surgeon to shape staple bridge 10 in order to conform to the anatomy of the patient. With this form of the invention, delivery device 35 can be used to deform/shape staple bridge 10. When a staple of this configuration has a force applied to its bridge 10 so that staple legs 15 are pivoted so as to be parallel to each other, malleable bridge 10 is plastically deformed so as to take a set (FIG. 21). The more staple legs 15 are opened (i.e., pivoted outboard), the more staple bridge 10 is plastically deformed. Upon insertion of the strained staple 5 into the prepared fracture site, elastic hinges 20 attempt to return staple legs 15 to their original un-restrained state while staple bridge 10 remains deformed (FIG. 22), thereby generating a compressive load and maintaining that compressive load across the fracture line while healing occurs. A staple of this configuration may be beneficial for the treatment of fractures where the anatomy is uneven (e.g., in an Akin Osteotomy).

Additional Use for Staple Mounting Holes

Figure 23:
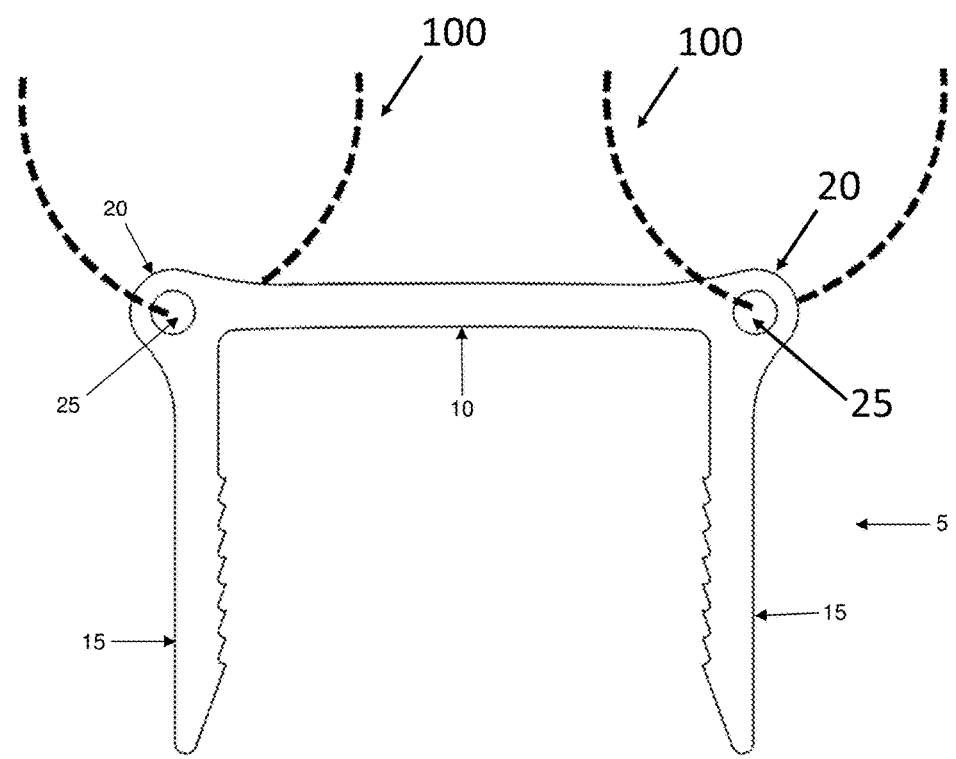
FIG. 23 shows how the holes at the hinge region of the staple may be used by the surgeon to attach sutures for tying down tissue (e.g., ligaments, tendons, etc.).

While holes 25 are primarily used for releasably mounting staple 5 to delivery device 35 (i.e., via pins 65), holes 25 also may be used after implantation to aid the surgeon with tying ligaments and/or tendons directly down to the bone (FIG. 23). Typically, a surgeon would use a suture anchor, bone tunnel or other method/device known in the art to re-secure a ligament and/or tendon to the bone. It should be appreciated that the staple of the present invention provides the surgeon with holes 25 which may be used to tie ligaments and/or tendons directly to the bone. This allows the surgeon to avoid having to use an additional implant or perform an additional procedure to achieve the same outcome.

Additional Applications

In the foregoing disclosure, novel staple 5 and novel delivery device 35 are discussed in the context of rejoining a broken bone. However, it should be appreciated that novel staple 5 and novel delivery device 35 may be used to promote joinder of substantially any two (or more) bone segments, e.g., they may be used to reduce openings and maintain compression between bone segments in osteotomies, or they may be used for inducing fusion across the bones of a joint in an arthrodesis, etc.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. An apparatus for securing tissue to a site in a human or animal body, the apparatus comprising:
   a staple comprising:
      a bridge configured to be elastically bendable;
      a first leg connected to the bridge by a first hinge region configured to be elastically bendable; and
      a second leg connected to the bridge by a second hinge region configured to be elastically bendable;
      wherein the first hinge region comprises a first hole and the second hinge region comprises a second hole; and wherein the bridge has a non-linear configuration when it is in an unstrained state, and wherein the first and second legs are angled toward one another when they are in an unstrained state; and at least one suture extending through (i) at least one of the first hole and the second hole, and (ii) the tissue to be secured to the site in a human or animal body.

2. An apparatus for generating, applying and maintaining compression to a site in a human or animal body, the apparatus comprising:

a staple comprising:
a bridge configured to be elastically bendable, wherein the bridge has a non-linear configuration when it is in an unstrained state, and further wherein when a delivery device applies a force to the bridge of the staple, the bridge is reconfigured from the non-linear configuration toward a linear configuration,
a first leg connected to the bridge by a first hinge region configured to be elastically bendable, wherein the first hinge region comprise a first hole configured to mate with a first element of the delivery device,
a second leg connected to the bridge by a second hinge region configured to be elastically bendable, wherein the second hinge region comprises a second hole configured to mate with a second element of the delivery device, and
wherein the first and second legs are angled toward one another when they are in an unstrained state;

the delivery device comprising:
the first element sized to be received in the first hole of the first hinge region of the staple,
the second element sized to be received in the second hole of the second hinge region of the staple,
a plunger adapted to apply the force to the bridge of the staple so as to reconfigure the bridge of the staple from the non-linear configuration toward the linear configuration, and
a body, wherein the first element is mounted to a first arm which is pivotally connected to the body, the second element is mounted to a second arm which is pivotally connected to the body, and the plunger is movably mounted to the body; and whereby, when the staple is mounted to the delivery device so that the first hole of the first hinge region mates with the first element of the delivery device and the second hole of the second hinge region mates with the second element of the delivery device, and when the delivery device applies the force to the bridge of the staple so as the reconfigure the bridge of the staple, the first and second legs are pivoted away from one another toward a parallel disposition.

3. An apparatus for generating, applying and maintaining compression to a site in a human or animal body, the apparatus comprising:

a staple comprising:
a bridge configured to be elastically bendable, wherein the bridge has a non-linear configuration when it is in an unstrained state, and further wherein when a delivery device applies a force to the bridge of the staple, the bridge is reconfigured from the non-linear configuration toward a linear configuration,
a first leg connected to the bridge by a first hinge region configured to be elastically bendable, wherein the first hinge region comprises a first hole configured to mate with a first element of the delivery device,
a second leg connected to the bridge by a second hinge region configured to be elastically bendable, wherein the second hinge region comprises a second hole configured to mate with a second element of the delivery, and
wherein the first and second legs are angled toward one another when they are in an unstrained state;

the delivery device comprising:
the first element sized to be received in the first hole of the first hinge region of the staple,
the second element sized to be received in the second hole of the second hinge region of the staple,
a plunger adapted to apply the force to the bridge of the staple so as to reconfigure the bridge of the staple from the non-linear configuration toward the linear configuration, wherein the plunger is moveably mounted to a body so as to allow the user to control the amount of force applied to the bridge of the staple, and whereby, when the staple is mounted to the delivery device so that the first hole of the first hinge region mates with the first element of the delivery device and the second hole of the second hinge region mates with the second element of the delivery device, and when the delivery device applies the force to the bridge of the staple so as to configure the bridge of the staple, the first and second legs are pivoted away from one another toward a parallel disposition.

4. A method for generating, applying and maintaining compression to a site in a human or animal body, the method comprising:

a) mounting a staple to a delivery device so that a first hole of a first hinge region mates with a first element of the delivery device and a second hole of a second hinge region mates with a second element of the delivery device, wherein
1) the staple comprises:
i) a bridge configured to be elastically bendable;
ii) a first leg connected to the bridge by the first hinge region configured to be elastically bendable, wherein the first hinge region comprises the first hole configured to mate with the first element of the delivery device, and
iii) a second leg connected to the bridge by the second hinge region configured to be elastically bendable, wherein the second hinge region comprises the second hole configured to mate with the second element of the delivery device, wherein the first and second legs are angled toward one another when they are in an unstrained state, and
2) the delivery device comprising:
i) the first element sized to the received in the first hole of the first hinge region of the staple,
ii) the second element sized to be received in the second hole of the second hinge region of the staple, and
iii) a plunger adapted to apply a force to the bridge of the staple so as to reconfigure the bridge of the staple, wherein the plunger is movable mounted to a body so as to allow the user to control the amount of force applied to the bridge of the staple;

b) applying the force to the bridge of the staple with the plunger of the delivery device so as to reconfigure the bridge of the staple such that the first and second legs are pivoted away from one another toward a parallel disposition, wherein the bridge has a non-linear configuration when it is in an unstrained state, and further wherein when the delivery device applies the force to the bridge of the staple, the bridge is reconfigured from the non-linear configuration toward a linear configuration;
c) inserting the staple into a site in a human or animal body;
d) withdrawing the plunger of the delivery device from the bridge of the staple so as to cause the staple to apply compression to the site in a human or animal body as the staple reconfigures; and
e) releasing the staple from the delivery device.

5. A method for generating, applying and maintaining compression to a site in a human or animal body, the method comprising:
a) mounting a staple to a delivery device so that a first hole of a first hinge region mates with a first element of the delivery device and a second hole of a second hinge region mates with a second element of the delivery device, wherein
   1) the staple comprises:
      i) a bridge configured to be elastically bendable;
      ii) a first leg connected to the bridge by the first hinge region configured to be elastically bendable, wherein the first hinge region comprises the first hole configured to mate with the first element of the delivery device, and
      iii) a second leg connected to the bridge by the second hinge region configured to be elastically bendable, wherein the second hinge region comprises the second configured to mate with the second element of the delivery device, wherein the first and second legs are angled toward one another when they are in an unstrained state, and
   2) the delivery device comprising:
      i) the first element sized to be received in the first hole of the first hinge region of the staple,
      ii) the second element sized to be received in the second hole of the second hinge region of the staple, and
      iii) a plunger adapted to apply a force to the bridge of the staple so as to reconfigure the bridge of the staple, wherein the plunger is movably mounted to a body so as to allow the user to control the rate at which the staple loads the site when the staple is inserted into site;
b) applying the force to the bridge of the staple with the plunger of the delivery device so as to reconfigure the bridge of the staple such that the first and second legs are pivoted away from one another toward a parallel disposition, wherein the bridge has a non-linear configuration when it is in an unstrained state, and further wherein when the delivery device applies the force to the bridge of the staple, the bridge is reconfigured from the non-linear configuration toward a linear configuration;
c) inserting the staple into a site in a human or animal body;
d) withdrawing the plunger of the delivery device from the bridge of the staple so as to cause the staple to apply compression to the site in a human or animal body as the staple reconfigures; and
e) releasing the staple from the delivery device.

6. A method for generating, applying and maintaining compression to a site in a human or animal body, the method comprising:
a) mounting a staple to a delivery device so that a first hole of a first region mates with a first element of the delivery device and a second hole of a second hinge region mates with a second element of the delivery device, wherein
   1) the staple comprises:
      i) a bridge configured to be elastically bendable;
      ii) a first leg connected to the bridge by the first hinge region configured to be elastically bendable, wherein the first hinge region comprises the first hole configured to mate with the first element of the delivery device, and
      iii) a second leg connected to the bridge by the hinge region configured to be elastically bendable, wherein the second hinge region comprises the second hole configured to mate with the second element of the delivery device, wherein the first and second legs and angled toward one another when they are in an unstrained state, and
   2) the delivery device comprising:
      i) the first element sized to be received in the first hole of the first hinge region of the staple,
      ii) the second element sized to be received in the second hole of the second hinge region of the staple, and
      iii) a plunger adapted to apply a force to the bridge of the staple so as to reconfigure the bridge of the staple,
b) applying the force to the bridge of the staple with the plunger of the delivery device so as to configure the bridge of the staple such that the first and second legs are pivoted away from one another toward a parallel disposition, wherein the bridge has a non-linear configuration when it is in an unstrained state, and further wherein when the delivery device applies the force to the bridge of the staple, the bridge is reconfigured from the non-linear configuration toward a linear configuration;
c) inserting the staple into a site in a human or animal body;
d) withdrawing the plunger of the delivery device from the bridge of the staple so as to cause the staple to apply compression to the site in a human or animal body as the staple reconfigures;
e) releasing the staple from the delivery device; and
f) removing the staple from the site by re-engaging the staple with the delivery device.

7. A method for generating, applying and maintaining compression to a site in a human or animal body, the method comprising:
a) mounting a staple to a delivery device so that a first hole of a first hinge region mates with a first element of the delivery device and a second hole of a second hinge region mates with a second element of the delivery, wherein
   1) the staple comprises:
      i) a bridge configured to be elastically bendable;
      ii) a first leg connected to the bridge by the first hinge region configured to be elastically bendable, wherein the first hinge region comprises the first hole configured to mate with the first element of the delivery device ,and
      iii) a second leg connected to the bridge by the second hinge region configured to be elastically bendable, wherein the second hinge region comprises the second hole configured to mate with the second element of the delivery device, wherein the first and second legs and angled toward one another when they are in an unstrained state, and
   2) the delivery device comprising:

i) the first element sized to be received in the first hole of the first hinge region of the staple, ii) the second element sized to be received in the second hole of the second hinge region of the staple, and iii) a plunger adapted to apply a force to the bridge of the staple so as to reconfigure the bridge of the staple, b) applying the force to the bridge of the staple with the plunger of the delivery device so as to reconfigure the bridge of the staple such that the first and second legs are pivoted away from one another toward a parallel disposition, wherein the bridge has a non-linear configuration when it is in an unstrained state, and further wherein when the delivery device applies the force to the bridge of the staple, the bridge is reconfigured from the non-linear configuration toward a linear configuration;

c) inserting the staple into a site in a human or animal body;

d) withdrawing the plunger of the delivery device from the bridge of the staple so as to cause the staple to apply compression to the site in a human or animal body as the staple reconfigures; and e) releasing the staple from the delivery device; and f) passing a suture through at least one of the first hole and the second hole and using the suture to secure tissue to the staple.

* * * * *

UNITED STATES PATENT AND TRADEMARK OFFICE
CERTIFICATE OF CORRECTION

PATENT NO. : 10,016,198 B2
APPLICATION NO. : 15/079770
DATED : July 10, 2018
INVENTOR(S) : Daniel Morgan et al.

It is certified that error appears in the above-identified patent and that said Letters Patent is hereby corrected as shown below:

In the Claims

In Claim 2, Column 13, Line 20; replace "region comprise a" with --region comprises a--

In Claim 3, Column 14, Line 3; replace "delivery, and" with --delivery device, and--

In Claim 4, Column 14, Line 50; replace "to the received" with --to be received--

In Claim 5, Column 15, Line 29; replace "the second configured" with --the second hole configured--

In Claim 5, Column 15, Line 44; replace "into site" with --into the site--

In Claim 6, Column 15, Line 66; replace "first region" with --first hinge region--

In Claim 6, Column 16, Line 15-16; replace "legs and angled" with --legs are angled--

In Claim 7, Column 16, Line 59; replace "the delivery device ,and" with --the delivery device, and--

In Claim 7, Column 16, Line 65; replace "legs and angled" with --legs are angled--

In Claim 7, Column 17, Line 24; delete "and" at the end of the line

Signed and Sealed this
First Day of February, 2022

Drew Hirshfeld
*Performing the Functions and Duties of the*
*Under Secretary of Commerce for Intellectual Property and*
*Director of the United States Patent and Trademark Office*